United States Patent [19]
Finkel et al.

[11] Patent Number: 5,976,819
[45] Date of Patent: Nov. 2, 1999

[54] PRODUCT AND PROCESS TO REGULATE ACTIN POLYMERIZATION IN T LYMPHOCYTES

[75] Inventors: Terri H. Finkel, Englewood; Moshe M. Rozdzial, Louisville, both of Colo.

[73] Assignee: National Jewish Medical and Research Center, Denver, Colo.

[21] Appl. No.: 08/563,892

[22] Filed: Nov. 21, 1995

[51] Int. Cl.⁶ .............................. C12Q 1/02; C12Q 1/68; G01N 33/50

[52] U.S. Cl. .............................. 435/7.24; 435/6; 435/29; 435/675

[58] Field of Search .................... 435/7.24, 975, 435/6, 29

[56] References Cited

U.S. PATENT DOCUMENTS

| | | | |
|---|---|---|---|
| 5,296,353 | 3/1994 | Ochoa et al. | 435/7.23 |
| 5,439,819 | 8/1995 | Littman et al. | 435/240.2 |
| 5,851,786 | 12/1998 | Johnson | 435/7.24 |

FOREIGN PATENT DOCUMENTS

| | | |
|---|---|---|
| 9417095 | 8/1994 | WIPO . |
| 9524915 | 9/1995 | WIPO . |

OTHER PUBLICATIONS

Rozdzial et al, Immunity, 3, 623–633, 1995.
A. Lanzavecchia, Science, 260, 937–944, 1993.
P. D. Phatak et al, Jour. Cell. Physiol., 159, 365–370, 1994.
H. Verschueren et al, Jour. Leuk. Biol., 55, 552–556, 1994.
A. Weiss, Cell, 73, 209–212, 1993.
Biomeda Corp. Catalogue, 1990, pp. 7, 15.
Caplan et al., 1995, *Proc. Natl. Acad. Sci. USA*, 92:4768–4772.
Finkel et al., *J. of Cellular Biochem.*, Supp. 18D, p. 399, Apr. 10–17, 1994 (Abstract—V556).
Valitutti et al., 1995, *J. Exp. Med.*, 181:577–584.
Braun et al., 1982, *J. Immunol.*, 128(3):1198–1204.
Flynn et al., 1993, *Mol. Cell. Biol.*, 13(12):7892–7900.
Furue et al., 1990, *J. Immunol.*, 144(2):736–739.
Hildebrand et al., 1993, *J. NIH Res.*, 5:49–54.
Parsey et al., 1993, *J. Immunol.*, 151(4):1881–1893.

*Primary Examiner*—David Saunders
*Attorney, Agent, or Firm*—Sheridan Ross P.C.

[57] ABSTRACT

The present invention relates to methods to regulate actin polymerization in T lymphocytes involved in tumorigenesis, inflammatory responses, immune responses, allergic responses and graft rejection responses, kits to perform such assays and methods to identify regulatory reagents that specifically control actin polymerization in T lymphocytes.

22 Claims, 5 Drawing Sheets

PRODUCT AND PROCESS TO REGULATE ACTIN POLYMERIZATION IN T LYMPHOCYTES

GOVERNMENT RIGHTS

This invention was made in part with government support under AI-30575A, AI-29903A and T-32A100048, all awarded by the National Institutes of Health. The government has certain rights to this invention.

FIELD OF THE INVENTION

The present invention relates to a process for regulating actin polymerization in T lymphocytes. The present invention also relates to assays and methods useful for identifying compounds that regulate actin polymerization in a T lymphocyte.

BACKGROUND OF THE INVENTION

Mammalian cells have cytoskeletal networks that are associated with their plasma membrane. The cytoskeleton is comprised of a dense network of actin filaments and associated actin-binding proteins. Components of both the cytoskeletal network and the plasma membrane are important for cellular signalling by, for example, localizing and focusing critical signalling molecules.

Certain mammalian cells comprise multichain surface receptors that enable a cell to respond to changes in the environment outside of the cell. One such multichain receptor is a T cell receptor (TCR) located on the surface of T lymphocytes. A TCR is a multichain, heteromeric structure composed of an antigen binding domain comprising $\alpha$ and $\beta$ chains, and non-covalently associated signal transducing complexes, including CD3-$\gamma$, $\delta$ and $\epsilon$ chains, and the $\zeta$ chains. Signal transduction events produced by TCR ligation with major histocompatibility complexes (MHC) induce a variety of cytoplasmic metabolic changes. For example, gene transcription and production of interleukin-2 (IL-2) are promoted by TCR ligation with MHC molecules.

Abnormalities in T lymphocyte function can arise through deregulation of signalling in T cells. Such diseases include, for example, autoimmune diseases, immunodeficiency diseases and immunoproliferative diseases. T lymphocyte function also contributes to graft rejection. To develop compounds that regulate the activity of molecules involved in T cell function, there must be an understanding of the molecules and interactions involved in such T cell related diseases.

Prior investigators have suggested that ligand binding converts surface immunoglobulin (Ig) to a detergent insoluble form, and that Ig receptors subsequently undergo extensive degradation accompanied by the appearance of a detergent soluble membrane product (Braun et al., *J. Immunol.* 128:1198–1204, 1982). Parsey et al. (*J. Immunol.* 151:1881–1893, 1993) hypothesize about a connection between actin polymerization and the ability of immobilized anti-CD3 antibodies to stimulate changes in cell shape and F-actin morphology. Furthermore, the expression of four src-family genes associated with T cell activation was shown to be specifically blocked by cyclosporine (Furue et al., *J. Immunol.* 144(2):736–739, 1990). Prior investigators, however, have failed to teach or appreciate that actin polymerization in T lymphocytes is specifically regulated by the presence of a particular motif (i.e., an immunoreceptor tyrosine-based activation motif; ITAM) of a $\zeta$ chain or $\epsilon$ chain of a TCR.

Although therapeutics exist that regulate immune activity in an animal, problems have arisen due to the non-specific nature and harmful side effects of such drugs. Despite a long-felt need to discover compounds that specifically regulate T cell activity with minimal side-effects, the complexity and lack of understanding of signal transduction networks in a T cell has hindered the development of such compounds. The present invention offers a method and product that permits regulation of specific steps of a signal transduction pathway in cells having ITAM-containing receptors.

SUMMARY OF THE INVENTION

Despite the complexity of signal transduction networks in cells, the present invention provides for a method to regulate actin polymerization in T lymphocytes by controlling the step in the signalling pathway in which an ITAM of the $\zeta$ or $\epsilon$ chain of a TCR interacts with a tyrosine kinase and/or an adaptor molecule. The advantages arising from this invention include the specific regulation of a step in a T lymphocyte signalling pathway that can regulate T lymphocyte growth, differentiation, homing, proliferation and death. The present inventors are the first to appreciate the specific molecular interactions involved in the actin polymerization steps within a T lymphocyte, and thus, are the first to propose a method and product that targets this particularly important event within a T lymphocyte.

One aspect of the present invention includes a method to identify compounds capable of regulating actin polymerization in a T lymphocyte, comprising: (a) contacting a putative regulatory compound with a T lymphocyte having a T cell receptor chain selected from the group consisting of a zeta chain and an epsilon chain, to form a contacted lymphocyte; (b) combining the contacted lymphocyte with a molecule capable of inducing the phosphorylation of the zeta chain or the epsilon chain; and (c) assessing the ability of the putative regulatory compound to regulate actin polymerization in the lymphocyte. In particular, the method further comprising assessing the amount of interleukin-2 produced by the lymphocyte.

Another aspect of the present invention includes a method to regulate actin polymerization in a T lymphocyte, comprising contacting a T lymphocyte with an effective amount of a regulatory reagent that is capable of altering the activity of an immunoreceptor tyrosine-based activation motif (ITAM) of a $\zeta$ chain of a T cell receptor. A preferred ITAM to regulate using the present method comprises the amino acid sequence SEQ ID NO:1. Regulation of actin polymerization by the present method preferably alters a T lymphocyte function including growth, differentiation, homing, proliferation, apoptosis and anergy.

The present invention also includes a method to regulate actin polymerization in a T lymphocyte, comprising contacting a T lymphocyte with an effective amount of a regulatory reagent that alters the activity of an immunoreceptor tyrosine-based activation motif of an $\epsilon$ chain of a T cell receptor. A preferred ITAM to regulate using the present method comprises the amino acid sequence SEQ ID NO:2.

One embodiment of the present invention includes a cellular system where a src-family tyrosine kinase is contacted with a T cell receptor chain selected from the group consisting of a $\zeta$ chain and an $\epsilon$ chain that is regulated by said src-family tyrosine kinase, the improvement comprising regulating actin polymerization by contacting a T lymphocyte with a reagent capable of binding to a protein including a third ITAM of a $\zeta$ chain, an ITAM of an $\epsilon$ chain and an SH2 domain.

Another embodiment of the present invention includes a formulation capable of regulating actin polymerization in a T lymphocyte, the formulation comprising: (a) a regulatory reagent that alters the activity of a molecule including an immunoreceptor tyrosine-based activation motif of a ζ chain of a T cell receptor and an immunoreceptor tyrosine-based activation motif of a ε chain of a T cell receptor in a cell; and (b) a pharmaceutically acceptable carrier.

The present invention also includes a kit to identify compounds capable of regulating actin polymerization in a T lymphocyte, the kit comprising: (a) a cell comprising a T cell receptor chain selected from the group consisting of a ζ chain, an ε chain, and actin monomers; and (b) a means for detecting the polymerization of the actin monomers.

DETAILED DESCRIPTION OF THE INVENTION

Figure 1:
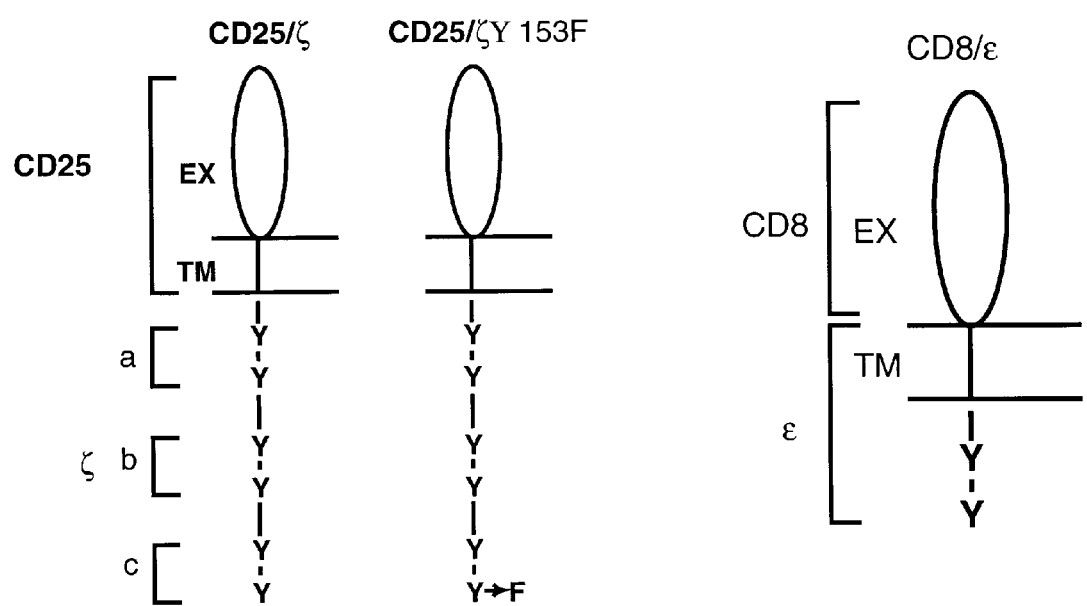
FIG. 1 illustrates the structure of CD25/ζ, CD25/ζY153F and CD8/ε chimeric molecules.

The present invention relates to a method for regulating actin polymerization in a T lymphocyte (i.e., T cell). Actin polymerization refers to the polymerization of actin monomers to form actin filaments. Actin filaments are one element of a cellular cytoskeleton. As used herein, the term "cytoskeleton" refers to a structure comprising protein fibers, including microfilaments comprising actin, microtubules and/or intermediate filaments. Particular structures of a cytoskeleton include stress fibers, and focal adhesions or adhesion plaques. A description of cellular cytoskeletons, and in particular actin filaments, can be found in Darnell et al. (*Molecular Cell Biology*, Scientific American Books, 1990, which is incorporated herein by reference in its entirety).

The polymerization and depolymerization of cytoskeletal filaments can be regulated by molecules involved in a signal transduction pathway in a cell. As used herein, the phrase "signal transduction pathway" refers to at least one biochemical reaction, but more commonly a series of biochemical reactions, which result from interaction of a cell with a stimulatory molecule. The interaction of a stimulatory molecule with a cell generates a "signal" that is transmitted through a signal transduction pathway, ultimately resulting in actin polymerization.

A signal transduction pathway of the present invention can involve a variety of signal transduction molecules that play a role in the transmission of a signal from one portion of a cell to another portion of the cell. As used herein, the term "molecule" refers to a protein, a lipid, a nucleic acid or an ion, and at times is used interchangeably with such terms. In particular, a signal transduction molecule refers to a protein, a lipid, a nucleotide, or an ion involved in a signal transduction pathway. Signal transduction molecules of the present invention include, for example, cell surface receptors and intracellular signal transduction molecules. As used herein, the phrase "cell surface receptor" includes molecules and complexes of molecules capable of receiving a signal and the transmission of such a signal across the plasma membrane of a cell. The phrase "intracellular signal transduction molecule," as used herein, includes those molecules or complexes of molecules involved in transmitting a signal from the plasma membrane of a cell through the cytoplasm of the cell, and in some instances, into the cell's nucleus. The phrase "stimulatory molecule", as used herein, includes ligands capable of binding to cell surface receptors to initiate a signal transduction pathway, as well as intracellular initiator molecules capable of initiating a signal transduction pathway from inside a cell.

One aspect of the present invention includes a method to regulate actin polymerization in a cell by controlling the activity of an immunoreceptor tyrosine-based activation motif (ITAM) contained in a protein expressed in such cell. Such ITAM's can be contained in a variety of proteins, in particular receptors that comprise multiple proteins referred to as multisubunit immune recognition receptors (MIRRs). MIRRs include receptors having multiple noncovalently associated subunits and are capable of interacting with tyrosine kinases. MIRRs can include, but are not limited to, T cell antigen receptors, B cell antigen receptors, Fc receptors and CD22. One example of an MIRR is a T cell receptor (TCR) on the surface of a T lymphocyte (used interchangeably herein with the term T cell). A TCR as referred to herein includes a multichain, heteromeric structure consisting of an antigen binding domain comprising an alpha (α) and a beta (β) chain, and non-covalently associated signal transducing complexes, CD3 and zeta (ζ) chains. TCRs are capable of binding to a ligand (as described in detail below) and are capable of initiating a signal transduction pathway in a cell upon ligand binding. A TCR typically includes an external portion located on the outer surface of a plasma membrane of a cell, a transmembrane portion that spans the plasma membrane, and a cytoplasmic portion located on the inner surface of the plasma membrane.

A suitable ITAM amino acid motif that can be regulated using a method of the present invention includes tyrosine, leucine and/or isoleucine residues having a spatial arrangement represented by an YXXLXXXXXXXYXXψ amino acid motif, wherein X can be any amino acid and "ψ" can be either leucine or isoleucine. A preferred ITAM that can be regulated using a method of the present invention includes the amino acid sequence E-R-R-R-G-K-G-H-D-G-L-Y-Q-G-L-S-T-A-T-K-D-T-Y-D-A-L (SEQ ID NO:1), N-K-E-R-P-P-P-V-P-N-P-D-Y-E-P-I-R-K-G-Q-R-D-L-Y-S-G-L (SEQ ID NO:2), E-T-A-A-N-L-Q-D-P-N-Q-L-Y-N-E-L-N-L-G-R-R-E-E-Y-D-V-L (SEQ ID NO:3), K-Q-Q-R-R-R-N-P-Q-E-G-V-Y-N-A-L-Q-K-D-K-M-A-E-A-Y-S-E-I (SEQ ID NO:4), E-R-R-R-G-K-G-H-D-G-L-Y-D-S-H-F-Q-A-V-Q-F-G-N-R-R-E-R-E (SEQ ID NO: 5), D-K-Q-T-L-L-Q-N-E-Q-L-Y-Q-P-L-K-D-R-E-Y-D-Q-Y-S-H-L (SEQ ID NO:6), E-V-Q-A-L-L-K-N-E-Q-L-Y-Q-P-L-R-D-R-E-D-T-Q-Y-S-R-L (SEQ ID NO:7), A-A-I-A-S-R-E-K-A-D-A-V-Y-T-G-L-N-T-R-N-Q-E-T-Y-E-T-L (SEQ ID NO:8), E-L-E-S-K-K-V-P-D-D-R-L-Y-E-E-L-N-H-V-Y-S-P-I-Y-S-E-L (SEQ ID NO:9), E-T-N-N-D-Y-E-T-A-D-G-G-Y-M-T-L-N-P-R-A-P-T-D-D-D-K-N-I-Y-L-T-L (SEQ ID NO:10), D-M-P-D-D-Y-E-D-E-N-L-Y-E-G-L-N-L-D-D-C-S-M-Y-E-D-I (SEQ ID NO: 11), D-A-G-D-E-Y-E-D-E-N-L-Y-E-G-L-N-L-D-D-C-S-M-Y-E-D-I (SEQ ID NO:12), D-G-K-A-G-M-E-E-D-H-T-Y-E-G-L-N-I-D-Q-T-A-T-Y-E-D-I (SEQ ID NO:13), D-S-K-A-G-M-E-E-D-H-T-Y-E-G-L-D-I-D-Q-T-A-T-Y-E-D-I (SEQ ID NO:14), D-R-Q-N-L-I-A-N-D-Q-L-Y-Q-P-L-G-E-R-N-D-G-Q-Y-S-Q-L (SEQ ID NO:15), P-E-I-S-L-T-P-K-P-D-S-D-Y-Q-A-L-L-P-S-A-P-E-I-Y-S-H-L (SEQ ID NO:16), D-Y-Q-A-L-L-P-S-A-P-E-I-Y-S-H-L-S-P-V-K-P-D-Y-I-N-L (SEQ ID NO:17), D-P-Y-W-G-N-G-D-R-H-S-D-Y-Q-P-L-G-T-Q-D-Q-S-L-Y-L-G-L (SEQ ID NO:18) and M-P-T-F-Y-L-A-L-H-G-G-Q-T-Y-H-L-I (SEQ ID NO:19), with an ITAM having the amino acid sequence SEQ ID NO:1 or SEQ ID NO:2 being even more preferred.

The term "activity" refers to any stage of activation of a signal transduction molecule by, for example, binding of a target or substrate molecule, a conformational change of a molecule which results in the acquisition of catalytic activity by the molecule; the phosphorylation of a molecule, thereby resulting in the acquisition or loss of catalytic activity by the molecule; or the translocation of a molecule from one region of a cell to another, thereby enabling the molecule to bind another molecule. The term "regulate" refers to controlling the activity of a molecule and/or biological function, such as enhancing or diminishing such activity or function.

A suitable cell useful in the present method includes any cell comprising a protein having an ITAM. Cells for use with the present invention include mammalian, invertebrate, fungal, yeast and bacterial cells. Preferably cells for use with the present invention include mammalian cells and more preferably human cells. Particularly preferred cells for use with the present method include T cells and B lymphocytes (B cells).

One embodiment of the present invention is a method to regulate actin polymerization in a T cell, comprising contacting a T cell with an effective amount of a regulatory reagent that is capable of altering the activity of an ITAM of a zeta (ζ) chain of a TCR. Another embodiment of the present invention is a method to regulate actin polymerization in a T cell, comprising contacting a T cell with an effective amount of a regulatory reagent that alters the activity of an ITAM of an epsilon (ε) chain of a TCR. According to the present invention, altering the activity of an ITAM includes-either enhancing or reducing the activity of the ITAM depending upon the desired effect. For example, if the present method is employed to treat immunodeficiency or tumor anergy, then the method is performed to enhance ITAM activity. If the present method is employed to treat graft rejection, then the method is performed to reduce ITAM activity. Suitable cells for use with the present invention include any cell that has a ζ chain or an ε chain in a native physiological context (e.g., mature T cells, immature T cells, T lymphomas; leukemias, natural killer cells, natural killer lymphomas and natural killer leukemias). A ζ chain refers to the ζ subunit of a TCR complex (described in detail below). An ε chain refers to an ε subunit from a CD3 complex. A CD3 complex consists of γ, δ and ε chains.

According to the present invention, the present method is useful for the regulation of actin polymerization in mature and immature T cells. A mature T cell is defined as a T cell having either CD4 or CD8 expression in conjunction with high levels of TCR expression. An immature T Cell can be a thymocyte at any stage prior to formation of a mature thymocyte (e.g., a T cell that does not express either CD4 or CD8 known as a double-negative cell; or a T cell that expresses both CD4 and CD8 known as a double-positive cell).

Effective amounts of a regulatory reagent can comprise an amount that regulates actin polymerization to an extent such that a biological function of a cell that is controlled by actin polymerization is modified. For example, an effective amount can comprise an amount that prevents actin polymerization an extent that a T cell no longer secretes interleukin-2 (IL-2). The amount of the regulatory agent can vary depending upon the type of regulatory reagent being administered to the cell and the type of cell. For example, the ease with which the regulatory reagent can cross the plasma membrane of a cell will dictate the effective concentration of the reagent (e.g., more reagent being necessary if transport across a membrane is impaired, etc.).

A suitable regulatory reagent, or a mimetope thereof, of the present invention is capable of altering the activity of an ITAM of a protein. In particular, a regulatory reagent, or a mimetope thereof, is capable of regulating T lymphocyte function, including growth, differentiation, proliferation, apoptosis, anergy and/or homing, more preferably IL-2 production. As used herein, anergy refers to the diminished reactivity by a T cell to an antigen and apoptosis refers to cell death. As used herein, homing refers to the movement of a T lymphocyte in response to a molecule. For example, a T cell can home to a site of inflammation in response to molecules secreted by cells involved in the inflammatory response.

Preferably, a regulatory reagent, or a mimetope thereof, is capable of regulating the activity of an ITAM by, for example, altering the interaction between an ITAM and its substrate; altering the binding between an ITAM and its target molecule; or altering the enzymatic activity of a target molecule that binds to an ITAM and phosphorylates the ITAM. As used herein, "altering the binding" can refer to altering the affinity of one molecule for another, blocking the situs of binding between two molecules, or interfering with the delivery of a molecule to the area of another molecule or allosterically altering a molecule so that it has either enhanced or diminished binding abilities. A "target molecule" refers to a molecule that can activate a signal transduction molecule by binding to the signal transduction molecule. A "substrate molecule" refers to a molecule acted upon by a signal transduction molecule. More preferably, a regulatory reagent, or mimetope thereof, binds to an ITAM; to a src homology region 2 (SH2) domain of a src-family kinase, syk-family kinase, adaptor molecule, PI-3 kinase or a 14-3-3 protein; to a src homology 3 (SH3) domain specific for proline-rich sequences or non-proline-rich sequences; to oligoproline containing actin binding proteins; to other actin binding proteins containing SH2 and/or SH3 domains; to plextrin homology domains (PH); to GLGF domains; or to WD domains.

A suitable regulatory reagent of the present invention includes a full or partial protein-based compound, a carbohydrate-based compound, a lipid-based compound, a nucleic acid-based compound, a natural organic compound, a synthetically derived organic compound or an antibody. A preferred regulatory reagent includes a peptide, a polypeptide or an antibody.

A preferred peptide, or a mimetope thereof, of the present invention comprises an ITAM amino acid motif as described in detail herein and/or an SH2 domain. A more preferred peptide, or a mimetope thereof, of the present invention comprises an SH2 domain of a protein, including Fyn, Lck, Zap-70, Shc, IRS-1, Nck, GRB-2, Syk, Yes, Hck, fak-B, PI-3 kinase and 14-3-3, with an SH2 domain of a protein, including Fyn, Lck, Zap-70, Shc, Syk, fak-B and 14-3-3 being more preferred.

Particularly preferred peptides, or mimetopes thereof, of the present invention include sequences comprising at least a portion of an SH2 amino acid sequence described in Pelliuci et al. (*Cell* 70:93–104, 1992), Chan et al. (*Cell* 71:649–662, 1992), Olivier et al. (*Cell* 73:179–191, 1993), Taniguchi et al. (*J. Biol. Chem.* 266:15790–15794, 1991), Sabe et al. (*Proc. Natl. Acad. Sci.* USA 89:2190–2194, 1992) and Koch et al. (*Science* 252:668–673, 1991).

In another embodiment, a regulatory reagent of the present invention is a peptide, or a mimetope thereof, of the present invention as described herein that is phosphorylated. Preferably, a peptide is phosphorylated on a tyrosine residue. Examples of phosphorylated peptides of the present invention, in which "Y(P)" represents a phosphorylated tyrosine residue, include E-R-R-R-G-K-G-H-D-G-L-Y(P)-Q-G-L-S-T-A-T-K-D-T-Y-D-A-L (SEQ ID NO:20), E-R-R-R-G-K-G-H-D-G-L-Y-Q-G-L-S-T-A-T-K-D-T-Y (P) -D-A-L (SEQ ID NO:21), E-R-R-R-G-K-G-H-D-G-L-Y(P) -Q-G-L-S-T-A-T-K-D-T-Y (P)-D-A-L (SEQ ID NO:22); N-K-E-R-P-P-P-V-P-N-P-D-Y(P)-E-P-I-R-K-G-Q-R-D-L-Y-S-G-L (SEQ ID NO:23), N-K-E-R-P-P-P-V-P-N-P-D-Y-E-P-I-R-K-G-Q-R-D-L-Y (P)-S-G-L (SEQ ID NO:24) and N-K-E-R-P-P-P-V-P-N-P-D-Y(P)-E-P-I-R-K-G-Q-R-D-L-Y(P)-S-G-L (SEQ ID NO:25).

In one embodiment, a regulatory reagent of the present invention includes an antibody that binds specifically to a 'signal transduction molecule in such a manner that the activity of the molecule is altered. A preferred antibody useful as a regulatory reagent of the present invention binds specifically to a protein, including but not limited to Fyn, Lck, Zap-70, Shc, IRS-1, Nck, GRB-2, Syk, Yes, Hck, fak-B, PI-3 kinase or 14-3-3. Another preferred antibody useful as a regulatory reagent of the present invention binds specifically to a protein including, for example, proteins that sequester actin monomers (e.g., profilin); proteins that control nucleation of an actin polymer (e.g., villin); proteins that block the barbed end of an actin polymer (e.g., fragmin); proteins that block the pointed end of an actin polymer (e.g., β-actin); proteins that sever an actin filament (e.g., gelsolin); proteins that depolymerize an actin polymer (e.g., depactin); or focal adhesion kinase, paxillin, tensin, annexin, ezrin, clathrin-H chain, vinculin, talin, zixin, cortactin, AFAP-110, p120, β catenin, connexin43 and cadherins.

In accordance with the present invention, a "mimetope" refers to any compound that is able to mimic the ability of a regulatory reagent of the present invention. A mimetope can be a peptide that has been modified to decrease its susceptibility to degradation but that still retains regulatory activity. Other examples of mimetopes include, but are not limited to, protein-based compounds, carbohydrate-based compounds, lipid-based compounds, nucleic acid-based compounds, natural organic compounds, synthetically derived organic compounds, anti-idiotypic antibodies and/or catalytic antibodies, or fragments thereof having desired regulatory activity. A mimetope can be obtained by, for example, screening libraries of natural and synthetic compounds for compounds capable of regulating actin polymerization in a T cell, as disclosed herein. A mimetope can also be obtained by, for example, rational drug design. In a rational drug design procedure, the three-dimensional structure of a compound of the present invention can be analyzed by, for example, nuclear magnetic resonance (NMR) or x-ray crystallography. The three-dimensional structure can then be used to predict structures of potential mimetopes by, for example, computer modelling. The predicted mimetope structures can then be produced by, for example, chemical synthesis, recombinant DNA technology, or by isolating a mimetope from a natural source (e.g., plants, animals, bacteria and fungi).

Another aspect of the present invention includes a formulation comprising a regulatory reagent of the present invention and a pharmaceutically acceptable carrier. As used herein, the term "a" can refer to at least one (i.e., one or more). A formulation of the present invention can include a regulatory reagent that is capable of regulating actin polymerization in a T cell, resulting in regulation of T cell function. Preferably, a formulation of the present invention comprises a combination of one or more peptides as described herein, or mimetopes thereof; a combination of antibodies as described herein, or mimetopes thereof; or a combination of antibodies and peptides as described herein, or mimetopes thereof.

As used herein, a "pharmaceutically acceptable carrier" refers to any substance suitable as a vehicle for delivering a regulatory reagent of the present invention to a suitable in vitro or in vivo site of action. As such, carriers can act as a pharmaceutically acceptable excipient or formulation of a therapeutic composition containing a regulatory reagent of the present invention. Preferred carriers are capable of maintaining a regulatory reagent of the present invention in a form that is capable of altering signal transduction in a cell. Examples of such carriers include, but are not limited to water, phosphate buffered saline, Ringer's solution, dextrose solution, serum-containing solutions, Hank's solution and other aqueous physiologically balanced solutions. Aqueous carriers can also contain suitable auxiliary substances required to approximate the physiological conditions of the recipient, for example, by enhancing chemical stability and isotonicity. Suitable auxiliary substances include, for example, sodium acetate, sodium chloride, sodium lactate, potassium chloride, calcium chloride, and other substances used to produce phosphate buffer, Tris buffer, and bicarbonate buffer. Auxiliary substances can also include preservatives, such as thimerosal, m- and o-cresol, formalin and benzol alcohol. Preferred auxiliary substances for aerosol delivery include surfactant substances non-toxic to a recipient, for example, esters or partial esters of fatty acids containing from about six to about twenty-two carbon atoms. Examples of esters include, caproic, octanoic, lauric, palmitic, stearic, linoleic, linolenic, olesteric, and oleic acids. Formulations of the present invention can be sterilized by conventional methods and/or lyophilized.

Useful carriers for a regulatory reagent of the present invention include any artificial or natural lipid-containing target molecule, preferably cells, cellular membranes, liposomes, and micelles. Preferably, formulations of the present invention are administered in the form of liposomes or micelles. Liposome and micelles of the present invention are capable of delivering a regulatory reagent from the extracellular space of a cell to the intracellular space of a cell. Concentrations of a regulatory reagent of the present invention combined with a liposome or a micelle include concentrations effective for delivering a sufficient amount of the regulatory reagent to a cell such that signal transduction in such cell is regulated.

A formulation of the present invention comprises at least one of the regulatory reagents of the present invention as described above and may also include at least one additional compound capable of regulating signal transduction. In one embodiment, a formulation of the present invention includes at least one isolated ITAM peptide and any other drug used for blocking actin polymerization or depolymerizing actin polymers in a cell. Examples of compounds capable of disrupting actin polymerization include cytochalasins; proteins that sequester actin monomers (e.g., profilin); proteins that control nucleation of an actin polymer (e.g., villin); proteins that block the barbed end of an actin polymer (e.g., fragmin); proteins that block the pointed end of an actin polymer (e.g., β-actin); proteins that sever an actin filament (e.g., gelsolin); proteins that depolymerize an actin polymer (e.g., depactin); and compounds that regulate the activity of a protein including, focal adhesion kinase, paxillin, tensin, annexin, ezrin, clathrin-H chain, vinculin, talin, zixin, cortactin, AFAP-110, p120, β catenin, connexin43 and cadherins.

It is within the scope of the invention that isolated nucleic acid molecules that encode a regulatory reagent of the present invention as herein disclosed can be used to produce such reagents. Methods to create and use such nucleic acid molecules are known to those of skill in the art. For example, a nucleic acid molecule encoding a peptide of the present invention can be chemically synthesized based on the amino acid sequence of the peptide, ligated into an expression vector and transformed into cells to produce a desired peptide.

A nucleic acid molecule as described herein can be DNA, RNA, or hybrids or derivatives of either DNA or RNA. Nucleic acid molecules as referred to herein can include regulatory regions that control expression of the nucleic acid molecule (e.g., transcription or translation control regions), full-length or partial coding regions, and combinations thereof. It is to be understood that any portion of a nucleic acid molecule can be produced by: (1) isolating the molecule from its natural milieu; (2) using recombinant DNA technology (e.g., PCR amplification, cloning); or (3) using chemical synthesis methods. A gene includes all nucleic acid sequences related to a signalling molecule, such as regulatory regions that control production of a cell surface receptor encoded by that gene (such as, but not limited to, transcription, translation or post-translation control regions) as well as the coding region itself.

A nucleic acid molecule can include functional equivalents of natural nucleic acid molecules encoding a protein. Functional equivalents of natural nucleic acid molecules can include, but are not limited to, natural allelic variants and modified nucleic acid molecules in which nucleotides have been inserted, deleted, substituted, and/or inverted in such a manner that such modifications do not substantially interfere with the nucleic acid molecule's ability to encode a molecule of the present invention. Preferred functional equivalents include sequences capable of hybridizing under stringent conditions (i.e., sequences having at least about 70% identity), to at least a portion of a signal transduction protein encoding nucleic acid molecule according to conditions described in Sambrook et al., ibid.

As guidance in determining what particular modifications can be made to any particular nucleic acid molecule, one of skill in the art should consider several factors that, without the need for undue experimentation, permit a skilled artisan to appreciate workable embodiments of the present invention. For example, such factors include modifications to nucleic acid molecules done in a manner so as to maintain particular functional regions of the encoded proteins including, a ligand binding site, a target binding site, a kinase catalytic domain, etc. Functional tests for these various characteristics (e.g., ligand binding studies and signal transduction assays such as kinase assays, and other assays described in detail herein and those known by those in the art) allows one of skill in the art to determine what modifications to nucleic acid sequences would be appropriate and which would not.

Transformation of a heterologous nucleic acid molecule (e.g., a heterologous cell surface receptor encoding a nucleic acid molecule) into a cell suitable for use in the present invention can be accomplished by any method by which a gene is inserted into a cell. Transformation techniques include, but are not limited to, transfection, retroviral infection, electroporation, lipofection, bacterial transfer and spheroplast fusion. Nucleic acid molecules transformed into cells suitable for use in the present invention can either remain on extra-chromosomal vectors or can be integrated into the cell genome.

Expression of a nucleic acid molecule of the present invention in a cell can be accomplished using techniques known to those skilled in the art. Briefly, the nucleic acid molecule is inserted into an expression vector in such a manner that the nucleic acid molecule is operatively joined to a transcription control sequence in order to be capable of effecting either constitutive or regulated expression of the gene when the gene is transformed into a host cell. Construction of desired expression vectors can be performed by methods known to those skilled in the art and expression can be in eukaryotic or prokaryotic systems. An expression system can be constructed from control elements, including transcription control sequences, translation control sequences, origins of replication, and other regulatory sequences that are compatible with a host cell, operatively linked to nucleic acid sequences using methods known to those of skill in the art. (see, for example, Sambrook et al., ibid.).

One aspect of the present invention includes a cell-based assay to identify compounds, referred to herein as "putative regulatory compounds", which are capable of regulating actin polymerization in a T cell. As used herein, the term "putative" refers to compounds having an unknown or previously unappreciated regulatory activity in a particular process. As such, the term "identify" is intended to include the particular selection of any compound, the usefulness of which as a regulatory compound of actin polymerization is determined by a method of the present invention.

One embodiment of the present invention relates to a method to identify a putative regulatory compound that regulates actin polymerization in a T cell, comprising: (1) contacting a putative regulatory compound with a T cell having a T cell receptor chain including a ζ chain and an ε chain, to form a "contacted cell"; (2) combining the contacted cell with a molecule capable of inducing the phosphorylation of the ζ chain or the ε chain; and (3) assessing the ability of the putative regulatory compound to regulate actin polymerization in the cell.

Suitable cells for use with the present invention include mammalian, invertebrate, plant, insect, fungal, yeast and bacterial cells. Preferably cells for use with the present invention include mammalian cells, more preferably human, non-human primate, mouse, rat, sheep and pig cells, and even more preferably mouse and human cells. More preferred cells include T lymphocytes, with murine and human T cell lines, murine and human T cell clones, with murine and human T cell hybridomas being even more preferred. In a preferred embodiment, putative regulatory compounds are identified using Jurkat, HPB, cells expressing CD25 conjugated to a full length ζ chain (e.g., MM-16.11, MM-16.12, MM-16.2 and MM-16.5), cells expressing CD25 conjugated to a ζ chain that lacks the first tyrosine residue in each ITAM (e.g., MM-17.1, MM-17.12, 17.2 17.4), cells expressing CD25-ζY153F (SEQ ID NO:31) (e.g., MM-18.2, MM-18.4, MM-18.6 and MM-18.7), cells expressing CD25 conjugated to a full length ε chain (e.g., 17.1 and 17.2), cells expressing CD8 conjugated to a full length ζ chain (e.g., 122.26), cells expressing CD8 conjugated to a ζ chain that lacks residues 95–163 (e.g., T91.10), cells expressing CD8 conjugated to a ζ chain that lacks residues 66–100 and 129–161 (e.g., B21), cells expressing CD8 conjugated to a ζ chain that lacks residues 67–126 (e.g., 5.6.4), cells expressing CD8-ζY153E (SEQ ID NO:30) (e.g., 910.7), cells expressing CD8-ζY153F (e.g., 78.12), CD25-ζ, CD8-ζ and CD8-ε chimeric molecules described in Wegener et al. (ibid.), HL-60, H-9, peripheral T cells, PBMC cells, lymph node T cells, splenic T cells, thymocytes, intraepithelial lymphocytes (IEL) and tumor infiltrating lymphocytes (TIL).

Alternatively, cells for use with the present invention can include spontaneously occurring variants of normal cells, or genetically engineered cells, that have altered signal transduction activity, such as enhanced responses to particular ligands. Signal transduction variants of normal cells can be identified using methods known to those in the art. For example, variants can be selected using fluorescence activated cell sorting (FACS) based on the level of calcium mobilization by a cell in response to a ligand. Genetically engineered cells can include recombinant cells of the present invention (described in detail below) that have been transformed with, for example, a recombinant molecule encoding a signal transduction molecule of the present invention.

In certain embodiments, a cell of the present invention is transformed with at least one heterologous nucleic acid molecule. Preferred nucleic acid molecules with which to transform a cell include, but are not limited to, a nucleic acid molecule encoding a chimeric protein comprising a portion of a CD25 molecule peptide bonded to a portion of a ζ chain (CD25-ζ), a portion of a CD8 molecule peptide bonded to a portion of a ζ chain (CD8-ζ), a portion of a CD25 molecule peptide bonded to a portion of a ε chain (CD25-ε) and a portion of a CD8 molecule peptide bonded to a portion of a ε chain (CD8-ε). Preferred cell lines of the present invention include Jurkat or BW-51-47 cells transfected with nucleic acid molecules encoding such CD25-ζ or CD8-ζ chain, and CD25-ε or CD8-ε chimeric molecules.

In another embodiment, a cell suitable for use in the present invention has one or more intracellular signal transduction molecules capable of transmitting a signal through the cytoplasm of the cell, resulting in actin polymerization. An intracellular signal transduction molecule as described herein can be produced in a cell by expression of a naturally occurring gene and/or by expression of a heterologous nucleic acid molecule transformed into the cell.

A preferred cell of the present invention has, amongst other signal transduction molecules, tyrosine kinases and adaptor molecules. Suitable tyrosine kinases of the present invention include a tyrosine kinase capable of regulating the activity of a ζ or ε chain, such as enhancing or limiting the ability of a ζ chain to induce calcium release in a cell. Calcium release or mobilization refers to measurable increases in intracellular calcium in a cell. Calcium release can be measured using methods known to those skilled in the art and generally described in Finkel et al. (*Nature* 330:6144–6146, 1987). Preferred tyrosine kinases of the present invention include src-family tyrosine kinases and syk-family tyrosine kinases. More preferred tyrosine kinases include Zap-70, Syk, Fyn, Lck, Yes, Hck, fak-B and PI-3 kinase. As used herein, adaptor molecules enable two other proteins to form a complex (e.g., a three molecule complex). Preferred adaptor molecules of the present invention includes Shc, IRS-1, Nck and GRB-2, with Shc being more preferred. A preferred cell of the present invention also includes other signalling molecules, preferably 14-3-3 and CSK.

A preferred cell of the present invention further comprises actin binding proteins including, but not limited to, focal adhesion kinase, paxillin, tensin, annexin, ezrin, clathrin-H chain, vinculin, talin, zixin, profilin, fractinin, cortactin, AFAP-110, p120, β catenin, connexin43 and cadherins.

Putative compounds as referred to herein include, for example, compounds that are products of rational drug design, natural products and compounds having partially defined signal transduction regulatory properties. A putative compound can be a protein-based compound, a carbohydrate-based compound, a lipid-based compound, a nucleic acid-based compound, a natural organic compound, a synthetically derived organic compound, an anti-idiotypic antibody and/or catalytic antibody, or fragments thereof. A putative regulatory compound can be obtained, for example, from libraries of natural or synthetic compounds, in particular from chemical or combinatorial libraries (i.e., libraries of compounds that differ in sequence or size but that have the same building blocks; see for example, U.S. Pat. Nos. 5,010,175 and 5,266,684 of Rutter and Santi, which are incorporated herein by reference in their entirety) or by rational drug design.

In a rational drug design procedure, the three-dimensional structure of a compound, such as a signal transduction molecule can be analyzed by, for example, nuclear magnetic resonance (NMR) or x-ray crystallography. This three-dimensional structure can then be used to predict structures of potential compounds, such as putative regulatory compounds by, for example, computer modelling. The predicted compound structure can then be produced by, for example, chemical synthesis, recombinant DNA technology, or by isolating a mimetope from a natural source (e.g., plants, animals, bacteria and fungi). Potential regulatory compounds can also be identified using SELEX technology as described in, for example, PCT Publication Nos. WO 91/19813; WO 92/02536 and WO 93/03172 (which are incorporated herein by reference in their entirety).

In particular, a naturally-occurring intracellular signal transduction molecule can be modified based on an analysis of its structure and function to form a suitable regulatory compound. For example, a compound capable of regulating the activity of an ITAM can comprise a compound having similar structure to an ITAM, a tyrosine kinase, an adaptor molecule, 14-3-3 or CSK. Additionally, a compound capable of interferin with the association of an ITAM with a target molecule can comprise a compound having similar structure to an ITAM, a SH2 domain of a tyrosine kinase, an adaptor molecule, 14-3-3 or CSK.

The conditions under which a cell of the present invention is contacted with a putative regulatory compound, such as by mixing, are conditions in which the cell can form actin polymers if essentially no other regulatory compounds are present that would interfere with actin polymerization. Achieving such conditions is within the skill in the art, and includes an effective medium in which the cell can be cultured such that the cell can exhibit cytoskeletal rearrangement. For example, for a mammalian cell, effective media are typically aqueous media comprising Dulbecco's modified Eagle's medium containing 10% fetal calf serum. Cells of the present invention can be cultured in a variety of containers including, but not limited to, tissue culture flasks, test tubes, microtiter dishes, and petri plates. Culturing is carried out at a temperature, pH and carbon dioxide content appropriate for the cell. Such culturing conditions are also within the skill in the art. For example, for Jurkat cells, culturing can be carried out at 37° C., in a 5% $CO_2$ environment.

Acceptable protocols to contact a cell with a putative regulatory compound in an effective manner include the method of contact, the number of cells per container contacted, the concentration of putative regulatory compound(s) administered to a cell, the incubation time of the putative regulatory compound with a cell, the concentration of stimulatory molecules administered to a cell, and the incubation time of the stimulatory molecules with a cell. Determination of such protocols can be accomplished by those skilled in the art based on variables such as the size of the container, the volume of liquid in the container, the type of cell being tested and the chemical composition of the putative regulatory compound (i.e., size, charge etc.) being tested.

Preferred methods for contacting a cell include electroporation, microinjection, cellular expression (i.e., using an expression system including naked nucleic acid molecules, recombinant virus, retrovirus expression vectors and adenovirus expression), use of ion pairing agents and use of detergents for cell permeabilization.

A suitable number of cells to be used with the present method includes a number of cells that enables one to detect a change in cytoskeletal structure using a detection method of the present invention (described in detail below). A more preferred number of cells includes between about 1 and $1 \times 10^6$ cells per well of a 96-well tissue culture dish. Following addition of the cells to the tissue culture dish, the cells can be pre-incubated at 37° C., 5% $CO_2$ for between about 0 to about 72 hours.

A suitable amount of putative regulatory compound(s) that is sufficient to regulate the activity of a signal transduction molecule inside the cell such that the regulation is detectable using a detection method of the present invention is electroporated into the cells using methods standard in the art based on the type of putative regulatory compound and the type of recipient cell. A preferred amount of putative regulatory compound(s) comprises between about 1 nM to about 10 mM of putative regulatory compound(s) per well of a 96-well plate.

In another embodiment of the method of the present invention, cells suitable for use in the present invention are stimulated with stimulatory molecules capable of binding to cell surface receptors of the present invention to initiate a signal transduction pathway and create a cellular response. Preferably, cells are stimulated with a stimulatory molecule following contact of a putative regulatory compound with a cell. Suitable stimulatory molecules can include, for example, hormones, growth factors, antigens, peptides, ions, other differentiation agents and other cell-type specific mitogens. Preferred stimulatory molecules include, but are not limited to, an antibody specific for a T cell receptor, an antibody specific for a $\zeta$ chain, an antibody specific for an $\epsilon$ chain, mitogens, lectins and major histocompatibility molecules associated with an antigenic peptide, and mixtures thereof. Particularly preferred stimulatory molecules of the present invention include, an antibody specific for a T cell receptor, an antibody specific for a $\zeta$ chain, an antibody specific for an $\epsilon$ chain, and mixtures thereof. A suitable amount of stimulatory molecule to add to a cell depends upon factors such as the type of ligand used (e.g., monomeric or multimeric; permeability, etc.) and the receptor being targeted (e.g., abundance of the receptor on a cell and the number of ligand binding sites/receptor). Preferably, between about 1 microgram ($\mu$g) and about 5 $\mu$g of ligand is added to about $1 \times 10^6$ cells.

The cells are allowed to incubate under standard conditions (based upon, for example, time, pH, etc.) for a suitable length of time to allow the stimulatory molecule to stimulate a signal transduction pathway. A preferred incubation time is between about 30 seconds to about 24 hours.

The method of the present invention includes determining if a putative regulatory compound is capable of regulating actin polymerization. Such methods include: actin polymerization analysis; cellular analysis; and performing protein phosphorylation or activation assays.

In one embodiment, the method of the present invention comprises detecting actin polymerization in a cell by determining alteration in a cell contacted with a putative regulatory compound, compared with a cell that has not been contacted with the same compound. For example, to measure the effectiveness of a putative regulatory compound for controlling actin polymerizations, one can observe the adhesiveness, growth, shape and motility characteristics of contacted and uncontacted cells. The extent of adhesiveness of a cell can be determined by whether a cell can be dislodged from a substratum by shaking or knocking the culture surface, or whether enzyme treatment, such as trypsin, is required to dislodge a cell from a substratum. Methods to dislodge cells from culture surfaces are well known in the art. Changes in cell growth can be determined by: counting the number of live cells after a certain period of time (by, for example, trypan blue staining or hoerscht staining); by determining the extent of tritiated thymidine uptake by a cell; by determining the amount of cytokine secretion by a cell (e.g., measuring IL-2 secretion); and/or by measuring the size of a cell after a certain period of time. Changes in cell shape can be determined by viewing cells to assess the flattening of cells on a substratum and/or the formation of cellular extensions, such as pseudopodium, filopodium and lamellipodium. Changes in cell motility can be determined by viewing the direction and distance a cell has traveled on a substratum during a certain period of time. Typically, such movement is associated with the formation of cellular extensions.

In another embodiment, the method of the present invention comprises detecting actin polymerization in a cell by determining changes in actin polymerization and/or organization. In such a method, the extent of actin polymerization and/or the organization of actin filaments are compared in cells contacted with a putative regulatory compound and cells not contacted with such a compound. The actin filaments are visualized by contacting the cells with labelled phalloidin (e.g., rhodamine conjugated phalloidin), which binds specifically to F-actin, using methods described herein (see, Example 1 below). Alternatively, actin filaments can be visualized using labelled antibodies that specifically bind to actin monomers or polymers, using methods known to those in the art. Additional methods include visualizing actin polymerization by electron microscopy, falling ball viscometry, spectrophotometry and sedimentation.

In yet another embodiment, the method of the present invention comprises detecting actin polymerization in a cell by determining association with and modulation of signal transduction proteins including, but not limited to, focal adhesion kinase, paxillin, tensin, annexin, ezrin, clathrin-H chain, vinculin, talin, zixin, profilin, fractinin, cortactin, AFAP-110, p120, β catenin, connexin43, cadherins, PI-3Kα, TCR, Syk, Zap-70, Fyn, Shc, IRS-1, Nck, GRB-2, Lck, VAV, GAP, Raf, Ras, MEK, MEKK, MAPK, p38, JNKK, JNK, jun-B, PLA2, JAK1, JAK2, JAK3, Tyk1, Tyk2, STATs, Myc, Jun, Ets-1, Elk-i, CREB, ATF-2, Yes, Hck, Src, CaM Kinase II, S6-K, sphingomyelinase, casein kinase, PKC, PI-3Kγ, SOS, CD45, HCP, Ssp, Syp, PLCγ1, PLCγ2, PLCβ1, PLCβ2, PLCβ3, PLCβ4, PLA2, Grb2, C5aR, IL-8R, MIP1αR, MIP1βR, MCP-1R, MCP-3R, PAFR, FMLPR, LTB$_4$R, GRPR, Fas receptor, Fas ligand, NFκ-B, SHP-76, N-FAT, AP-1, CD7, CD5, tumor necrosis factor receptor, CD40 ligand, CD28, CD2, integrins and addressins. As used herein, modulation of a signal transduction protein refers to, for example, the phosphorylation of a molecule or the association of a molecule to another signalling molecule. One method to determine modulation of a signal transduction molecule is to determine the phosphorylation state of the molecule using methods and reagents known to those of skill in the art. For example, phosphorylation can be detected using antibodies specific for phosphorylated amino acid residues. Alternatively, polymerized actin can be isolated by sedimentation and the actin-associated proteins can be identified.

Alternatively, the method of the present invention includes determining if a putative regulatory compound is capable of regulating T cell function. Such methods include determining IL-2 production by a T cell; and assessing T cell apoptosis, growth, adhesion, differentiation, proliferation and/or homing.

The method of the present invention is particularly useful for regulating actin polymerization in cells involved in diseases, including, but not limited to, tumorigenesis, immunoproliferative diseases, immunodeficiency diseases, cancers, autoimmune diseases, infectious diseases, allergic responses and graft rejection. In particular, the present method protects an animal from diseases including, for example, rheumatoid arthritis, SLE, vasculitis, scleroderma, solid tumors, hematopoietic malignancies, acute and chronic graft rejection, AIDS, asthma and allergic rhinitis.

Another aspect of the present invention includes a kit to identify compounds capable of regulating actin polymerization, in a cell, such actin polymerization involving in some respect, ζ and/or ε chains of a TCR. Such a kit includes: (a) a cell comprising a T cell receptor chain selected from the group consisting of a ζ chain, an ε chain, and actin monomers; and (b) a means for detecting the polymerization of such actin monomers. Such a means for detecting actin polymerization are described in detail herein and are known to those of skill in the art. Suitable cells for use with a kit of the present invention include cells described in detail herein. A preferred cell for use with a kit includes, Jurkat, HPB, MM-16.11, MM-16.12, MM-16.2, MM-16.5, 17.1, 17.2, 122.26, HL-60, H-9, peripheral T cells, PBMC cells, lymph node T cells, splenic T cells, thymocytes, intraepithelial lymphocytes (IEL) and tumor infiltrating lymphocytes (TIL).

The present invention also includes the determination as to whether a putative regulatory compound is capable of regulating a biological response in a mammal. Such a method entails administering a putative regulatory compound to an animal, such compound being shown, using an assay of the present invention, to regulate actin polymerization in a cell. Such a determination is useful for determining conditions under which a putative regulatory compound can be administered to an animal as a formulation of the present invention. In particular, a putative regulatory compound can be administered to an animal to determine if the compound is capable of regulating, for example, an immune response, an allergic response and/or graft rejection in the animal. Acceptable protocols to administer putative regulatory compounds to test the effectiveness of the compound include individual dose size, number of doses, frequency of dose administration, and mode of administration. Determination of such protocols can be accomplished by those skilled in the art. A suitable single dose is a dose that is capable of altering a biological response in an animal when administered one or more times over a suitable time period (e.g., from minutes to days or weeks). Preferably, a dose comprises from about 1 nanogram of the compound per kilogram of body weight (ng/kg) to about 1 gram of compound per kilogram of body weight (gm/kg), more preferably 100 ng/kg to about 100 milligrams/kilogram (mg/kg), and even more preferably from about 10 micrograms of compound per kilogram of body weight to about 10 mg/kg. Modes of administration can include, but are not limited to, intraarticular, intraperitoneal, subcutaneous, rectally, intradermal, intravenous, nasal, oral, transdermal and intramuscular routes. A putative regulatory compound can be combined with other components such as a pharmaceutically acceptable carrier as described in detail herein, prior to administration to an animal.

In another aspect of the present invention, the present invention includes conducting a toxicity test on an animal to determine the toxicity of a putative regulatory compound. Toxicity tests for putative regulatory compounds can be performed, for example, on animals after a putative regulatory compound has been determined to have an effect at the cellular level on signal transduction, such as the regulation of cellular inflammatory responses. Such toxicity tests are within the skill of the art, and generally involve testing the toxicity of a compound in vivo or in vitro. A suitable method for testing the toxicity of a putative regulatory compound in vivo can involve scientifically controlled administration of the putative regulatory compound to a number of animals and a period of observance in which the effects of the compound on various aspects of the animal's biological functions (e.g., occurrence of tissue damage, functioning of organs and death) are noted. Suitable methods for testing the toxicity of a putative regulatory compound in vitro can involve scientifically controlled administration of the putative regulatory compound to a cell and subsequent measurement of cell function, cytotoxicity, or cell death. Cell function can be measured by any one of a wide range of assays which will be apparent to one of skill in the art, several of which are herein disclosed (e.g., tyrosine phosphorylation, calcium mobilization, proliferation and cytokine secretion assays). Methods to measure cytotoxicity are well known in the art and include measurement of the ability to reduce chromogenic substrates such as the tetrazolium-based MTT or sulphorhodamine blue, ATP-bioluminescence assays and fluorescence assays, for example using the Fluorescent Green Protein, among many other readily available assays (see, for example, Bellamy, Drugs 44(5):690–708, 1992, which is incorporated herein by reference in its entirety). Methods to measure cell death include, for example, coomassie blue staining, acridine orange staining, terminal deoxynucelotidyl transferase (TDT) assays for measuring DNA fragmentation, neutral red exclusion, and measuring changes in forward light scatter in a flow cytometer.

Another aspect of the present invention comprises administering to an animal a formulation capable of regulating actin polymerization. A formulation of the present invention is particularly useful for preventing or treating diseases involving abnormal T cell activity, growth or migration.

An effective administration protocol (i.e., administering a formulation in an effective manner) comprises suitable dose parameters and modes of administration that result in prevention or treatment of a disease. Effective dose parameters and modes of administration can be determined using methods standard in the art for a particular disease. Such methods include, for example, determination of survival rates, side effects (i.e., toxicity) and progression or regression of disease. For example, the effectiveness of dose parameters and modes of administration of a formulation of the present invention can be determined by assessing response rates. Such response rates refer to the percentage of treated patients in a population of patients that respond with either partial or complete remission.

In accordance with the present invention, a suitable single dose size is a dose that is capable of preventing or treating an animal with a disease when administered one or more times over a suitable time period. Doses can vary depending upon the disease being treated. For example, in the treatment of cancer, a suitable single dose can be dependent upon whether the cancer being treated is a primary tumor or a metastatic form of cancer.

It will be obvious to one of skill in the art that the number of doses administered to an animal is dependent upon the extent of the disease and the response of an individual patient to the treatment. For example, in the case of cancer, a large tumor may require more doses than a smaller tumor. In some cases, however, a patient having a large tumor may require fewer doses than a patient with a smaller tumor, if the patient with the large tumor responds more favorably to the therapeutic composition than the patient with the smaller tumor. Thus, it is within the scope of the present invention that a suitable number of doses, as well as the time periods between administration, includes any number required to cause regression of a disease.

Formulations can be administered directly to a cell in vivo or ex vivo or systemically. Preferred methods of systemic administration, include intraarticular, intravenous injection, aerosol, oral and percutaneous (topical) delivery. Intravenous injections can be performed using methods standard in the art. Aerosol delivery can also be performed using methods standard in the art (see, for example, Stribling et al., Proc. Natl. Acad. Sci. USA 189:11277–11281, 1992, which is incorporated herein by reference in its entirety). Oral delivery can be performed by complexing a therapeutic composition of the present invention to a carrier capable of withstanding degradation by digestive enzymes in the gut of an animal. Examples of such carriers, include plastic capsules or tablets, such as those known in the art. Topical delivery can be performed by mixing a formulation of the present invention with a lipophilic reagent (e.g., DMSO) that is capable of passing into the skin.

The following examples are provided for the purposes of illustration and are not intended to limit the scope of the present invention.

EXAMPLES

Example 1

This example describes the association of TCR-ζ chain with the detergent insoluble cell fraction upon T cell receptor ligation.

A. Cell Activation and Lysis

Freshly isolated thymocytes or lymph node T cells from normal adult C57B1/6 mice were washed 3 times in BSS+ 5% fetal calf serum (FCS) and incubated in the presence or absence of an anti-pan-TCR-β (H57-597; hereafter referred to as anti-αβTCR antibody; Kubo et al., J. Immunol. 142:2736–2742, 1989) antibody at 5 μg/$10^6$ cells, and/or cross-linking goat anti-mouse antibody (obtained from Sigma Chemical Co., St. Louis, Mo.) at 20 μg/ml, for 30 min at 4° C., with at least two washes with BSS+5% FCS after each antibody incubation. The cells were then incubated for 15 min at 37° C., solubilized with 0.5% NP-40 in a Tris-buffered saline solution (TBS; 150 mM NaCl, 10 mM Tris, pH 7.3) containing protease and phosphatase inhibitors (0.2 mM $VO_3$, 10 mM NaF, 10 mM tetrasodium pyrophosphate, 1 mM PMSF, and 1 μg/ml each of Aprotinin, Leupeptin, and α-1-antitrypsin) and centrifuged at 10,000 rpm for 10 min to pellet the insoluble material.

Prior to separation by one-dimensional sodium dodecyl sulfate-polyacrylamide gel electrophoresis (SDS-PAGE), the insoluble cell pellet was resolubilized by boiling in non-reducing sample buffer. Immunoprecipitation of the detergent soluble fraction was performed with Sepharose-conjugated anti-TCR-ζ mAb (H146-968; Rozdzial et al., J. Immunol. 153:1563–1580, 1994).

B. Gel Electrophoresis and Immunoblotting

The proteins contained in the isolated pellet and the product of the anti-TCR-ζ immunoprecipitation performed in step A were boiled in non-reducing sample buffer and, at 1–5×$10^7$ cell equivalents/lane, were separated under non-reducing conditions by 10% SDS-PAGE gel electrophoresis. Electrophoretic transfer of protein to 0.2 μm nitrocellulose filters was performed in 48 mM Tris, 39 mM glycine, 1.3 mM SDS, and 20% methanol, at room temperature under constant current (150–200 mA) for 2 hrs. Efficiency of transfer was monitored by transfer of prestained markers, by reversible staining of the blots with Ponceau-S, and by silver staining of the electroeluted gels. The filters were then quenched in blotting buffer composed of 125 mM NaCl and 25 mM Tris, pH 7.6 (TS), and 5% skim milk, or with 5% crystallized bovine serum albumin (BSA). Following electrotransfer and quenching, the nitrocellulose filters were immunoblotted with specific antibodies (1 μg/ml) to TCR-ζ for 3 hr, and washed in TS-0.05% Tween-20. The washed filters were incubated with $^{125}$I-protein A (4×$10^5$ cpm/ml) in quenching buffer for 1 hr, and washed as above. The blots were then dried and exposed to Kodak XAR-2 film at −70° C.

C. Densitometry

Densitometric analysis (corrected for loading of unequal cell equivalents) was performed on the resulting immunoblots using a MacIntosh image scanner. The scans were than interfaced with a MacIntosh computer and densitometric analysis carried out using the NIH Image 1.49 program (NIH, Bethesda, Md.) for one-dimensional scanning.

D. Results

The results of the immunoblot analysis indicate that about 7% of TCR-ζ protein sedimented with the detergent insoluble pellet from resting thymocytes and lymph node T cells. Upon activation of thymocytes and lymph node T cells, an average of about 16% and about 43% of TCR-ζ protein, respectively, associated with the detergent insoluble pellet and was depleted from the supernatant relative to resting cells. The activation-induced association with the detergent insoluble pellet occurred with a concomitant depletion of TCR-ζ protein from the detergent soluble fraction. Treatment of thymocytes or lymph node T cells with the anti-TCR-ζ antibody or GAM alone did not substantially increase the amount of TCR-ζ in the pellet relative to untreated controls.

Thus, upon ligation of TCR, the amount of TCR-ζ in the detergent insoluble pellet increased an average of two-fold (16%) and six-fold (43%) compared with non-ligated samples. In comparison, in resting T cells, TCR-ζ protein was predominantly localized to the detergent soluble material. In addition, the amount of TCR-ζ in the insoluble pellet from activated lymph node T cells is significantly greater than that isolated from activated thymocytes.

Example 2

This example describes the association of CD8-ε chimeric proteins with the cytoskeleton upon TCR ligation.

A T cell hybridoma that expresses a CD8-ε chimeric molecule comprising a full-length ε chain was incubated in the presence or absence of an anti-CD8 antibody (53.6.72). Each sample was then incubated in the presence of a goat anti-rat antibody (GAR; obtained from Jackson Immuno Research Labs, West Grove, Pa.) to cross-link anti-CD8 antibody bound to the surface of the hybridomas. The cells were then lysed and immunoblots prepared as described in Example 1. Immunoblots were performed using anti-CD8 antibody.

The results indicate that a CD3-ε chain can associate with the insoluble pellet in response to TCR ligation. Thus, the ability to associate with the cytoskeleton is shared between different chains of the TCR.

Example 3

This example describes the association of TCR-ζ with cytoskeleton independent of other chains of the TCR.

Chimeric constructions were assembled by polymerase chain reaction (PCR) as described (Beaufils et al. *EMBO J.* 12:5105–5112, 1993). Sequences of the various PCR products were confirmed using the dideoxy-chain termination method. A first chimeric DNA construct, referred to herein as pCD25/ζ, comprises a nucleic acid molecule encoding the extracellular and transmembrane regions of CD25 ligated to a nucleic acid molecule encoding the cytoplasmic domain of TCR-ζ, cloned into a pSRa-neo expression vector. pCD25/ζ encodes for a protein referred to herein as CD25/ζ, which is illustrated in FIG. 1. Referring to FIG. 1, the a, b, and c regions represent the three ITAMs of the cytoplasmic domain of the TCR-ζ chain, each region having two tyrosines (Y).

A second chimeric DNA construct, referred to herein as pCD25/ζY153F, comprises a nucleic acid molecule identical to pCD25/ζ except the tyrosine at residue 153 was substituted for a phenylalanine (illustrated in FIGS. 1 and 2). pCD25/ζY153F encodes for a protein referred to herein as CD25/ζY153F.

pCD25/ζ and pCD25/ζY153F were transfected into the BW 5147 α-β-thymoma (described in White et al., *J. Immunol.* 143:1822–1825, 1989) and selected in the presence of G418-sulfate using the methods described in Wegener et al. (*Cell* 68:83–95, 1992).

The T cell hybridomas expressing CD25/ζ and CD25/ζY153F were incubated in the presence or absence of anti-CD25 antibody (obtained from AMAC, Inc., Westbrook, Me.). The cells were then incubated in the presence of GAR antibody to cross-link antibody-bound surface CD25. The samples were then lysed and immunoblotted using the methods described in Example 1. Immunoblots were performed using anti-TCR-ζ antibody or anti-phosphotyrosine antibody (obtained from Sigma Chemical Co., St. Louis, Mo.).

The results indicate that CD25/ζ associated with the detergent insoluble pellet in response to ligation of the extracellular domain of CD25. The results further indicate that CD25/ζY153F could not associate with the cytoskeleton. Thus, the results indicate that other components of the TCR are not required for the interaction of ζ with the cytoskeleton. Moreover, the results indicate that the tyrosine at residue 153 of the ζ chain is important for the association of the ζ chain to the cytoskeleton.

Example 4

This example describes the cytoskeletal component involved in TCR-ζ binding to the cytoskeleton upon TCR ligation.

Cleared lysates of resting and activated T cells were prepared using the method described in Example 1. TCR-ζ protein was precipitated from the detergent soluble fraction using the anti-TCR-ζ antibody described above. The resulting precipitate was resolved by SDS-PAGE gel electrophoresis and immunoblotted with either anti-actin antibody (kindly provided by Dr. B. Jockusch, Braunschweig, Germany) or anti-tubulin antibody (obtained from Sigma Chemical Co., St. Louis, Mo.) or anti-TCR-ζ antibody.

Based upon the immunoblot results, actin was shown to co-precipitate with TCR-ζ, but not tubulin. The association of actin with TCR-ζ increased significantly in response to TCR ligation, under conditions favoring cytoskeleton depolymerization (i.e., incubation in the presence of cytoskeletal poisons). In the absence of cytoskeletal poisons, binding of TCR-ζ protein to actin was not increased despite TCR ligation. These results indicate that activation induces a change, in TCR-ζ, actin or an intermediary molecule, that promotes the interaction between TCR-ζ and the cytoskeleton. The results also indicate that the actin which co-precipitated with TCR-ζ after TCR ligation separated at a slightly higher molecular weight than actin isolated from non-TCR ligated cells, thereby indicating that the actin has undergone posttranslational modification upon cell activation.

Together, these results demonstrate an association of TCR-ζ with microfilaments and regulation of this association by T cell activation. These data also indicate that actin monomers, dimers or short filaments contain a binding site for TCR-ζ interaction.

Example 5

This example describes the molecular mechanisms and structural interactions that mediate the association of TCR-ζ with the detergent insoluble pellet.

Lymph node T cells or hybridoma cells expressing pCD25/ζ described in Example 3 were incubated in 5 μg/ml cytochalasin D and nocodazole for 1.5 hrs before or after activation with, respectively, an anti-αβTCR antibody or anti-CD25 antibody and cross-linking GAM or GAR antibody. The cells were then lysed and both the detergent soluble and insoluble fractions were immunoblotted according to the methods described in Example 1. Immunoblots were performed using anti-actin antibody to detect the co-precipitation of actin with TCR/ζ or anti-TCR-ζ antibody.

A. Detergent Insoluble Fractions

Association of TCR-ζ with the detergent insoluble pellet was unaffected in resting and activated cells treated with cytochalasin D and nocodazole after activation, relative to untreated controls cell samples. TCR-ζ, however, did not associate with the detergent insoluble pellet in cells treated with cytochalasin D and nocodazol prior to activation. The data indicate a direct or indirect involvement of the cytoskeleton in the association between TCR-ζ and the detergent insoluble fraction. Cells treated with the cytoskeleton poisons consistently showed lower TCR-ζ-cytoskeleton association than unactivated controls.

B. Detergent Soluble Fractions

The results indicate that TCR-ζ remaining in the detergent soluble supernatant of samples co-immunoprecipitates with actin either in the presence or absence of cytochalasin D and nocodazol, under resting or activating conditions. The amount of soluble actin co-precipitating with TCR-ζ, under conditions of cytoskeletal depolymerization, increased significantly in cell lysates from activated relative to resting thymocytes.

Thus, the results indicate that treatment of the cells with cytoskeletal poisons disrupted association of TCR-ζ with the pellet in cells treated before, but not after TCR ligation. Partial disruption of the association of TCR-ζ with the pellet was also seen in thymocytes and peripheral lymph node T cells treated with cytoskeletal poisons, indicating involvement of the cytoskeleton, specifically microfilaments, in the interaction with TCR-ζ.

Example 6

This example describes the requirement for the third ITAM of TCR-ζ (SEQ ID NO:26) in the association of TCR-ζ with cytoskeleton.

Figure 2:
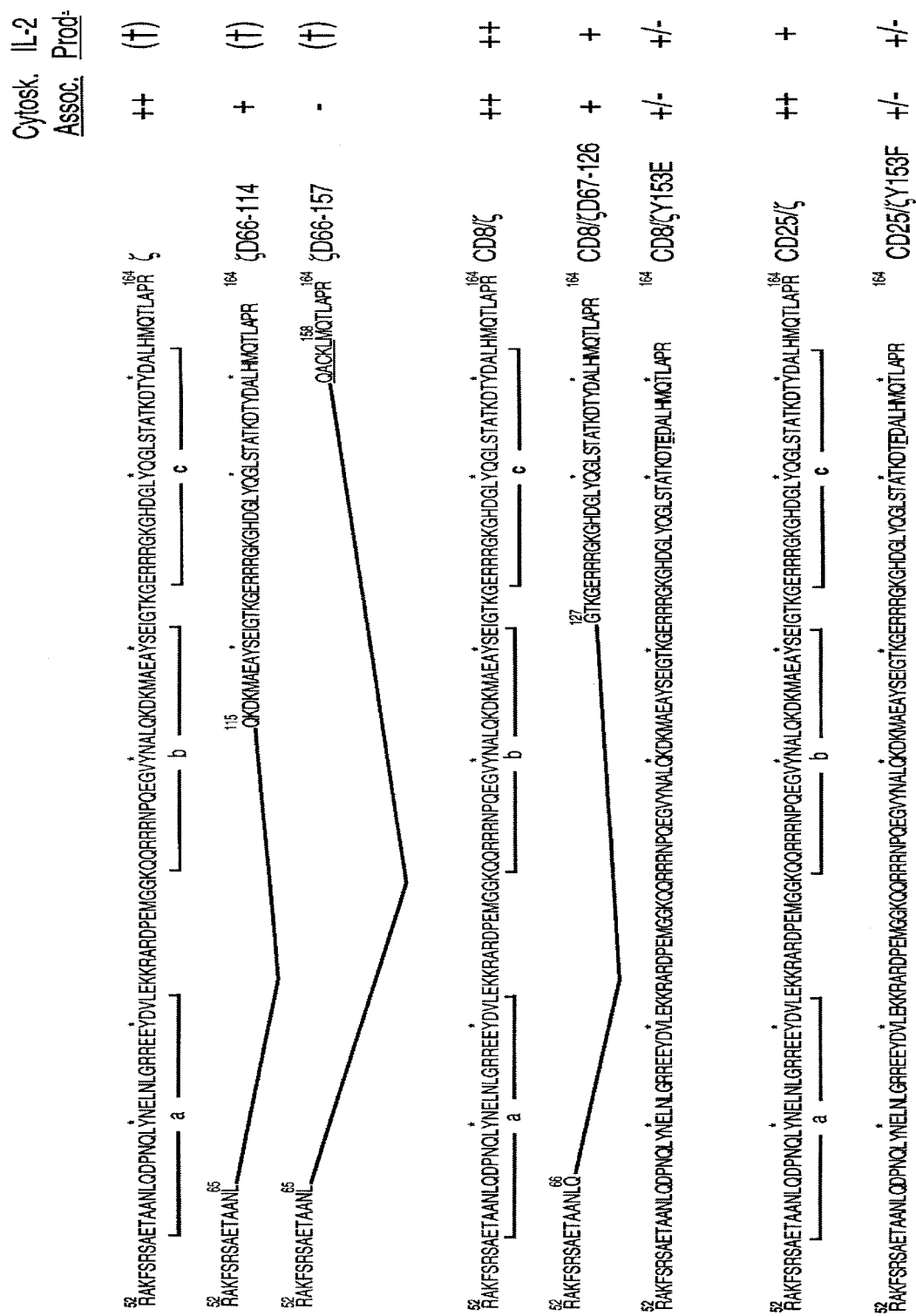
FIG. 2 illustrates the predicted structures of truncated TCR-C polypeptides, CD25/ζ and CD8/ε chimeric molecules.

BW 5147 α,β-thymoma cells transfected with truncated TCR-ζ (ζD66-114 (SEQ ID NO:27) deleted in residues 66–114; or ζD66-157 SEQ ID NO:28, deleted in residues 66–157; described in Wegener et al., ibid.; illustrated in FIG. 2) were incubated in the absence or presence of anti-αβTCR antibody and GAM, or GAM alone. The cells were then lysed and immunoblotted with anti-TCR-ζ antibody using the methods described in Example 1. The foregoing method was repeated in about 3 different experiments.

The results indicate that only the full length TCR-ζ and the truncated TCR-ζ encoded by the ζD66-114 construct (not expressing the first ITAM) associated with the cytoskeleton upon activation. The TCR-ζ encoded by the ζD66-157 construct did not associate with the cytoskeleton in response to TCR ligation. These results indicate that the region of TCR-ζ containing the ITAMs, rather than the membrane proximal or distal regions of the polypeptide, is required for cytoskeletal association.

Experiments were performed to confirm the requirement of the third ITAM for TCR-ζ association with cytoskeleton. BW 5147 α-β-thymoma cells transfected with a nucleic acid molecule encoding a truncated CD8/ζ chimera (CD8/ζD67-126 (SEQ ID NO:29), expressing only intact ζc domain; described in Wegener et al., ibid.; illustrated in FIG. 2) were stimulated, lysed and immunoblotted using the methods described immediately above. The results indicated that the CD8/ζ chimera containing only the third ITAM of the ζ chain associated with the cytoskeleton, thereby indicating that the third activation motif of TCR-ζ is sufficient for cytoskeletal association.

Example 7

This example describes the requirement for phosphorylation of the distal tyrosine of the third ITAM of TCR-ζ in cytoskeleton association.

Tyrosine phosphorylated proteins were detected in freshly isolated thymocytes or lymph node T cells from normal adult C57B1/6 mice and in CD25/ζ-expressing T cell hybridomas, incubated in the absence or presence of anti-αβTCR or anti-CD8-ε (145-2C11; Leo et al., Proc. Natl. Acad. Sci. USA 84:1374–1378, 1987; illustrated in FIGS. 1 and 2) antibodies and/or GAM, and lysed, as described in Example 1. Immunoprecipitation of the detergent soluble fraction was then performed, in series, with agarose-linked anti-phosphotyrosine antibody (Ab-1, Oncogene Science, Uniondale, N.Y.) and Sepharose-conjugated anti-TCR-ζ antibody (H146-968). Following electrotransfer, the nitrocellulose filters were immunoblotted with specific antibodies to TCR-ζ or phosphotyrosine (Ab-2, Oncogene Science, Uniondale, N.Y.).

As indicated in FIG. 1, each ITAM TCR-ζ of has two tyrosines. Analysis of the detergent insoluble pellet revealed an increase in tyrosine phosphorylated TCR-ζ in the pellets of activated compared to resting thymocytes and lymph node T cells. In addition, analysis of the CD25/ζ chimera after receptor ligation revealed an association of tyrosine-phosphorylated TCR-ζ with the cytoskeleton. The results indicate that inductive tyrosine phosphorylation precedes cytoskeletal association or, alternatively, occurs as a result of this association. Finally, results obtained using the CD8/ζY153F (described in Wegener et al., ibid. or CD25/ζY153F chimeras, which have substitutions of the distal, COOH-terminal tyrosine, indicated that the removal of the distal tyrosine almost completely abrogated cytoskeletal association, thereby indicating that tyrosine phosphorylation of the third ITAM plays a critical role in TCR-ζ association with the cytoskeleton.

Example 8

This example describes the association of tyrosine phosphorylated TCR-ζ with the actin cytoskeleton in a cell-free system.

Freshly isolated murine thymocytes or lymph node T cells, or CD25/ζ-expressing T cell hybridomas, were washed 3 times in BSS and incubated in the presence or absence of cytochalasin D for 1.5 hrs at 4° C., solubilized with 0.5% NP-40 in a Tris buffered saline solution (TBS; 150 mM NaCl, 10 mM Tris, pH 7.3) containing protease and phosphatase inhibitors (0.2 mM $VO_3$, 10 mM NaF, 1 mM PMSF, and 1 mg/ml each of Aprotinin, Leupeptin, and α-1-antitrypsin) and centrifuged at 10,000 rpm for 10.min to pellet the insoluble material. The detergent soluble fraction was then incubated with or without MgATP (0.5 mM $MgSO_4$ and 5 mM ATP), $Mg^{2+}$ or ATP alone, incubated at 37° C. for 15 min and centrifuged at 10,000 rpm for 10 min to pellet the newly polymerized material. To increase actin polymerization, the $Mg^{2+}$ concentration was increased to 2 mM. Certain samples were further incubated with 5M EDTA to chelate existing $Mg^{2+}$. Immunoprecipitation of the detergent soluble fraction with anti-TCR-ζ antibody was then performed as described in Example 4. The pellet and the anti-TCR-ζ immunoprecipitate were resolved by SDS-PAGE gel electrophoresis and immunoblotted with anti-TCR-ζ antibody.

The results indicated that the addition of exogenous MgATP induced the association of TCR-ζ with the detergent insoluble pellet and a corresponding depletion of TCR-ζ from solution was detected within 1 minute of incubation. Optimal association was determined by time course experiments to be after 10–15 minutes at 37° C., similar to that seen in intact cells after ligation of the TCR receptor (see Example 1). Almost no binding was observed at MgATP concentrations below 0.1 mM, whereas at 1 mM ATP and above, association of TCR-ζ with the lysis pellet appeared optimal. Results obtained using cell lysates incubated with $Mg^{2+}$ and/or ATP in the presence or absence of EDTA, indicated that the addition of $Mg^{2+}$ or nucleotide contributed to TCR-ζ precipitation in vitro. In the presence of 2 mM $Mg^{2+}$ alone, actin polymerization was induced in vitro without additional TCR-ζ binding, indicating that actin polymerization is not sufficient for TCR-ζ association.

The CD25/ζ chimera that co-sediments with the actin cytoskeleton in the in vitro activating (MgATP) condition was depleted from the pellet under actin depolymerizing conditions. In addition, the microfilament association of the CD25/ζ chimera was abrogated by the substitution of tyrosine 153 for phenylalanine. These data provide further evidence that the actin cytoskeleton is specifically involved in association with TCR-ζ in response to T cell activation. Furthermore, the results indicate that tyrosine phosphorylation in the third ITAM plays a critical role in this association.

Example 9

This example describes that the association of TCR-ζ to cytoskeleton is specific to mature T cells.

Unfractionated thymocytes from normal adult C57B1/6 mice were incubated or 30 min at 4° C. with a biotin-labeled anti-αβTCR antibody (H57-597), washed three times, labeled with streptavidin R-phycoerythrin (Tago, Inc., Burlingame, Calif.) for 10 min at 4° C., and sorted on a Coulter 751 flow cytometer at 4° C. to separate the immature (TCR$^{low}$) and mature (TCR$^{high}$) T cell populations. The mature and immature thymocytes were then analyzed and found to be 96% and 76% homogeneous, respectively.

Figure 3:
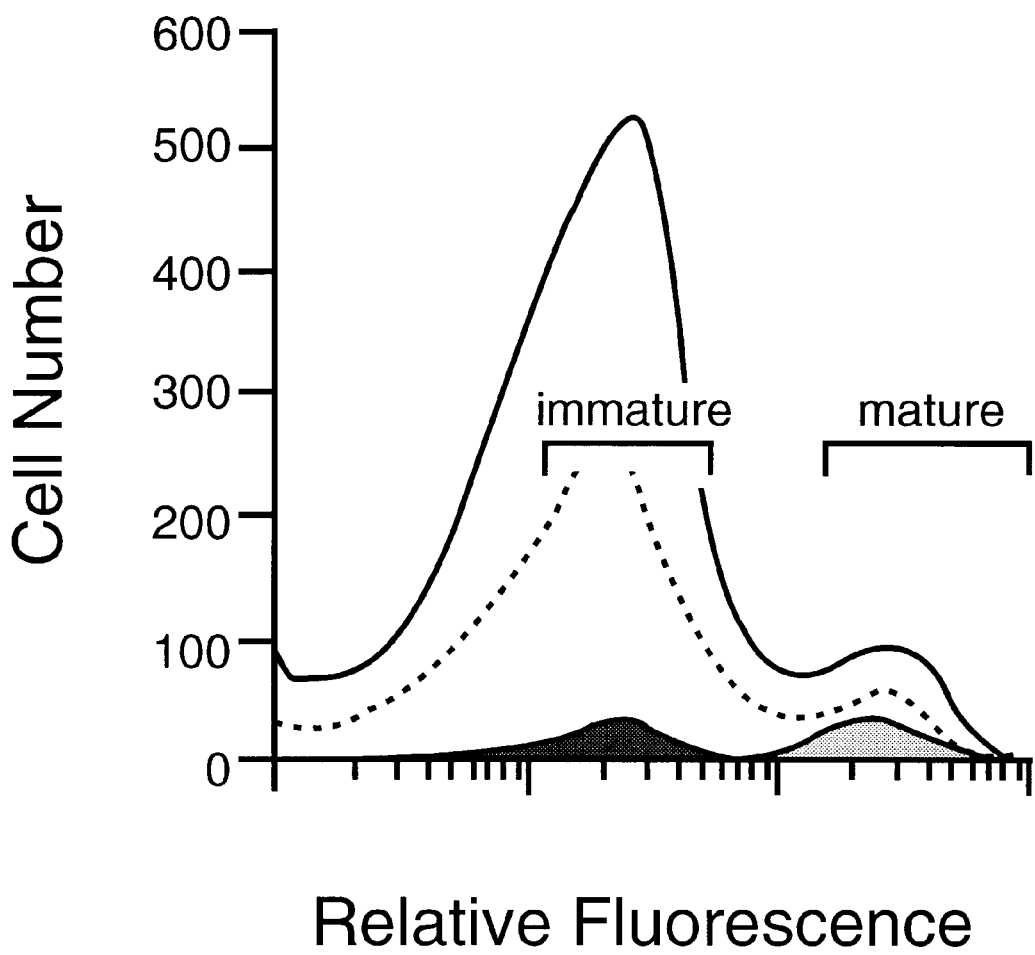
FIG. 3 illustrates flow cytometric profiles of mouse thymocytes labelled with fluorescent TCR specific antibodies.

Flow cytometric profiles of mouse thymocytes labeled with fluorescent anti-αβTCR (H57-597) antibody, before (---) sorting into subpopulations bearing low (dark gray) or high (light gray) antigen receptor levels are shown in FIG. 3. Receptor expression was not modulated during the course of the cell sort, as shown in the cross-linked, but unsorted, sample (—). Thus, conditions of TCR ligation that induce TCR-ζ-cytoskeleton association are not accompanied by receptor modulation from the cell surface.

Sorted populations were lysed according to the method described in Example 1, and the detergent insoluble pellets were immunoblotted with anti-TCR-ζ antibody. Despite analysis of eight times the cell equivalency of the other populations, ligation of the TCR receptor on immature thymocytes did not induce detectable association of TCR-ζ with the cytoskeleton. Most of the TCR-ζ from this immature population remained in solution.

Example 10

This example describes that the association of TCR-ζ with cytoskeleton is correlated with late events of T cell activation.

Microcultures of 0.25 ml were prepared containing $10^5$ responding T cells expressing CD8/ζ, CD8/ζD67-126, CD8/ζY153E, CD25/ζ or CD25/ζY153E. For stimulation, microtiter wells were precoated with 50 μl of a phosphate-buffered saline solution containing varying concentrations of purified anti-CD8-α antibody (19/178) or anti-hCD25 antibody (B1.49.9) to cross-link the CD8/ζ, CD8/ζD67-126 and CD8/ζY153E, or CD25/ζ and CD25/ζY153E, respectively, on the surface of the T cells. Control wells were coated with an irrelevant antibody. After 2 hours at room temperature and 1 hr at 4° C., the wells were washed three times with fetal calf serum-containing tissue culture medium. Control wells were coated with an irrelevant antibody. After 24 hours in culture, the supernatants were harvested and assayed for IL-2 content using methods generally described in Gillis et al. (*J. Immunol.* 120:2027–2032, 1978). A concentration of 1 U/ml of IL-2 was the minimum detectable in this assay.

Figure 4:
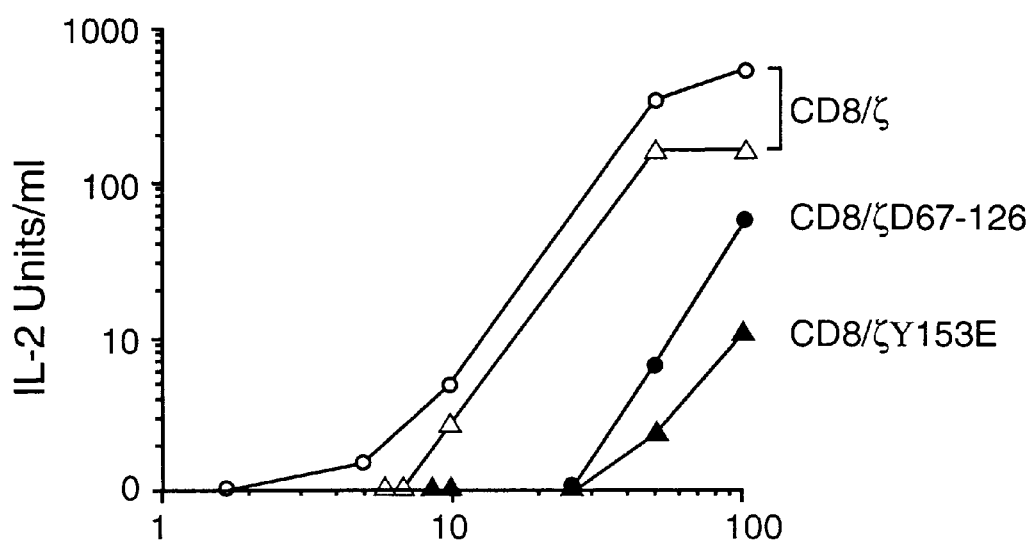
FIG. 4 illustrates IL-2 production by cells expressing CD8/ζ proteins in response to stimulation with antibodies specific for CD8-α.
Figure 5:
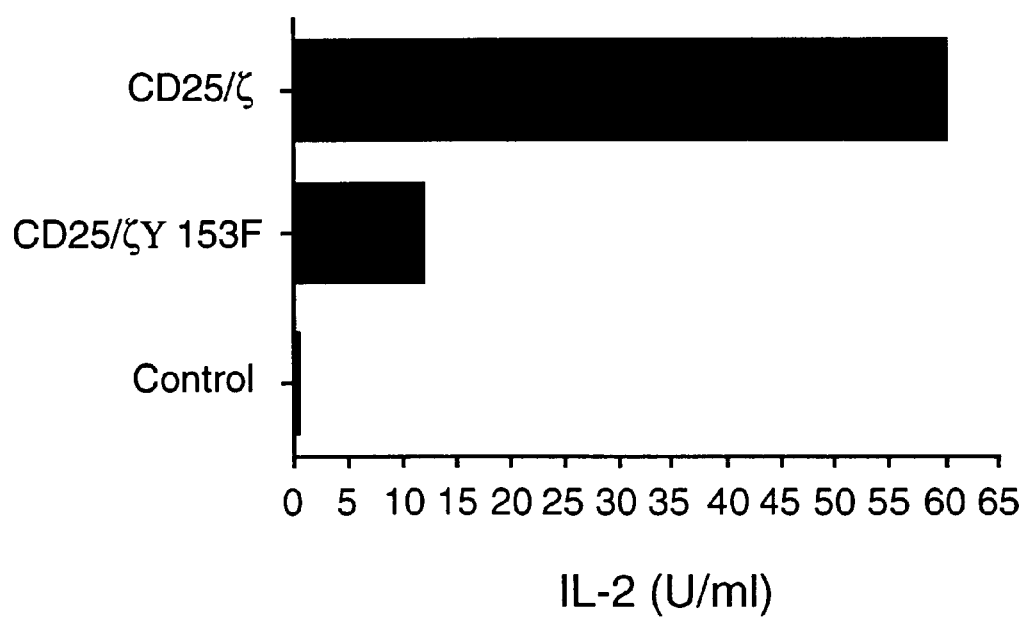
FIG. 5 illustrates IL-2 production by cells expressing CD25/ζ proteins in response to stimulation with antibodies specific for CD25.

The results indicate that IL-2 production correlates with TCR-ζ association with the cytoskeleton. Referring to FIG. 4, at maximal stimulation, cells expressing the deleted (CD8/ζD67-126; closed circles) and substituted (CD8/ζY153E; closed triangles) constructs produced, respectively, 40- and 100-fold less IL-2 than the wild-type CD8/ζ (open circles and triangles). Similar results were obtained using cells expressing CD25/ζY153F when compared with cells expressing wild-type CD25/ζ (FIG. 5). Interestingly, receptor ligation of the CD25/ζY153F construct induced tyrosine phosphorylation of a set of proteins that was qualitatively and quantitatively indistinguishable from that induced in the intact CD25/ζ chimera, indicating that decreased IL-2 production by CD25/ζY153F was not due to the inability of CD25/ζY153F to bind to and/or activate critical tyrosine kinases. These data show that cytoskeletal association by ITAM-containing motifs is correlated with late events of T cell activation.

SEQUENCE LISTING

The following Sequence Listing is submitted pursuant to 37 CFR §1.821. A copy in computer readable form is also submitted herewith.

Applicants assert pursuant to 37 CFR §1.821(f) that the content of the paper and computer readable copies of SEQ ID NO:1 through SEQ ID NO:25 submitted herewith are the same.

---

SEQUENCE LISTING (1) GENERAL INFORMATION:

(iii) NUMBER OF SEQUENCES: 31

(2) INFORMATION FOR SEQ ID NO:1:

(i) SEQUENCE CHARACTERISTICS:
        (A) LENGTH: 26 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:1:

```
Glu Arg Arg Arg Gly Lys Gly His Asp Gly Leu Tyr Gln Gly Leu Ser
 1               5                  10                  15
Thr Ala Thr Lys Asp Thr Tyr Ala Leu
                20                  25
```

(2) INFORMATION FOR SEQ ID NO:2:

(i) SEQUENCE CHARACTERISTICS:
        (A) LENGTH: 27 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:2:

```
Asn Lys Glu Arg Pro Pro Pro Val Pro Asn Pro Asp Tyr Glu Pro Ile
 1               5                  10                  15
Arg Lys Gly Gln Arg Asp Leu Tyr Ser Gly Leu
            20                  25
```

(2) INFORMATION FOR SEQ ID NO:3:

(i) SEQUENCE CHARACTERISTICS:
        (A) LENGTH: 27 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:3:

```
Glu Thr Ala Ala Asn Leu Gln Asp Pro Asn Gln Leu Tyr Asn Glu Leu
 1               5                  10                  15
Asn Leu Gly Arg Arg Glu Glu Tyr Asp Val Leu
            20                  25
```

(2) INFORMATION FOR SEQ ID NO:4:

(i) SEQUENCE CHARACTERISTICS:
        (A) LENGTH: 28 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:4:

```
Lys Gln Gln Arg Arg Arg Asn Pro Gln Glu Gly Val Tyr Asn Ala Leu
 1               5                  10                  15
Gln Lys Asp Lys Met Ala Glu Ala Tyr Ser Glu Ile
            20                  25
```

(2) INFORMATION FOR SEQ ID NO:5:

(i) SEQUENCE CHARACTERISTICS:
        (A) LENGTH: 28 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:5:

```
Glu Arg Arg Arg Gly Lys Gly His Asp Gly Leu Tyr Asp Ser His Phe
 1               5                  10                  15
Gln Ala Val Gln Phe Gly Asn Arg Arg Glu Arg Glu
            20                  25
```

(2) INFORMATION FOR SEQ ID NO:6:

(i) SEQUENCE CHARACTERISTICS:

(A) LENGTH: 26 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:6:

Asp Lys Gln Thr Leu Leu Gln Asn Glu Gln Leu Tyr Gln Pro Leu Lys
1               5                   10                  15

Asp Arg Glu Tyr Asp Gln Tyr Ser His Leu
            20                  25

(2) INFORMATION FOR SEQ ID NO:7:

(i) SEQUENCE CHARACTERISTICS:
        (A) LENGTH: 26 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:7:

Glu Val Gln Ala Leu Leu Lys Asn Glu Gln Leu Tyr Gln Pro Leu Arg
1               5                   10                  15

Asp Arg Glu Asp Thr Gln Tyr Ser Arg Leu
            20                  25

(2) INFORMATION FOR SEQ ID NO:8:

(i) SEQUENCE CHARACTERISTICS:
        (A) LENGTH: 27 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:8:

Ala Ala Ile Ala Ser Arg Glu Lys Ala Asp Ala Val Tyr Thr Gly Leu
1               5                   10                  15

Asn Thr Arg Asn Gln Glu Thr Tyr Glu Thr Leu
            20                  25

(2) INFORMATION FOR SEQ ID NO:9:

(i) SEQUENCE CHARACTERISTICS:
        (A) LENGTH: 27 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:9:

Glu Leu Glu Ser Lys Lys Val Pro Asp Asp Arg Leu Tyr Glu Glu Leu
1               5                   10                  15

Asn His Val Tyr Ser Pro Ile Tyr Ser Glu Leu
            20                  25

(2) INFORMATION FOR SEQ ID NO:10:

(i) SEQUENCE CHARACTERISTICS:
        (A) LENGTH: 32 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:10:

Glu Thr Asn Asn Asp Tyr Glu Thr Ala Asp Gly Gly Tyr Met Thr Leu
1               5                   10                  15

Asn Pro Arg Ala Pro Thr Asp Asp Lys Asn Ile Tyr Leu Thr Leu
            20                  25                  30

(2) INFORMATION FOR SEQ ID NO:11:

(i) SEQUENCE CHARACTERISTICS:
        (A) LENGTH: 26 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:11:

Asp Met Pro Asp Asp Tyr Glu Asp Glu Asn Leu Tyr Glu Gly Leu Asn
1               5                   10                  15

Leu Asp Asp Cys Ser Met Tyr Glu Asp Ile
            20                  25

(2) INFORMATION FOR SEQ ID NO:12:

(i) SEQUENCE CHARACTERISTICS:
        (A) LENGTH: 26 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:12:

Asp Ala Gly Asp Glu Tyr Glu Asp Glu Asn Leu Tyr Glu Gly Leu Asn
1               5                   10                  15

Leu Asp Asp Cys Ser Met Tyr Glu Asp Ile
            20                  25

(2) INFORMATION FOR SEQ ID NO:13:

(i) SEQUENCE CHARACTERISTICS:
        (A) LENGTH: 26 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:13:

Asp Gly Lys Ala Gly Met Glu Glu Asp His Thr Tyr Glu Gly Leu Asn
1               5                   10                  15

Ile Asp Gln Thr Ala Thr Tyr Glu Asp Ile
            20                  25

(2) INFORMATION FOR SEQ ID NO:14:

(i) SEQUENCE CHARACTERISTICS:
        (A) LENGTH: 26 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:14:

Asp Ser Lys Ala Gly Met Glu Glu Asp His Thr Tyr Glu Gly Leu Asp
1               5                   10                  15

Ile Asp Gln Thr Ala Thr Tyr Glu Asp Ile
            20                  25

(2) INFORMATION FOR SEQ ID NO:15:

(i) SEQUENCE CHARACTERISTICS:
        (A) LENGTH: 26 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:15:

Asp Arg Gln Asn Leu Ile Ala Asn Asp Gln Leu Tyr Gln Pro Leu Gly
1               5                   10                  15

Glu Arg Asn Asp Gly Gln Tyr Ser Gln Leu
            20                  25

(2) INFORMATION FOR SEQ ID NO:16:

(i) SEQUENCE CHARACTERISTICS:
        (A) LENGTH: 27 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:16:

Pro Glu Ile Ser Leu Thr Pro Lys Pro Asp Ser Asp Tyr Gln Ala Leu
1               5                   10                  15

Leu Pro Ser Ala Pro Glu Ile Tyr Ser His Leu
            20                  25

(2) INFORMATION FOR SEQ ID NO:17:

(i) SEQUENCE CHARACTERISTICS:
        (A) LENGTH: 26 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:17:

Asp Tyr Gln Ala Leu Leu Pro Ser Ala Pro Glu Ile Tyr Ser His Leu
1               5                   10                  15

Ser Pro Val Lys Pro Asp Tyr Ile Asn Leu
            20                  25

(2) INFORMATION FOR SEQ ID NO:18:

(i) SEQUENCE CHARACTERISTICS:
        (A) LENGTH: 27 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:18:

Asp Pro Tyr Trp Gly Asn Gly Asp Arg His Ser Asp Tyr Gln Pro Leu
1               5                   10                  15

Gly Thr Gln Asp Gln Ser Leu Tyr Leu Gly Leu
            20                  25

(2) INFORMATION FOR SEQ ID NO:19:

(i) SEQUENCE CHARACTERISTICS:
        (A) LENGTH: 17 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:19:

Met Pro Thr Phe Tyr Leu Ala Leu His Gly Gly Gln Thr Tyr His Leu
1               5                   10                  15
Ile (2) INFORMATION FOR SEQ ID NO:20:

(i) SEQUENCE CHARACTERISTICS:
        (A) LENGTH: 26 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:20:

Glu Arg Arg Arg Gly Lys Gly His Asp Gly Leu Tyr Gln Gly Leu Ser
1               5                   10                  15
Thr Ala Thr Lys Asp Thr Tyr Asp Ala Leu
            20                  25

(2) INFORMATION FOR SEQ ID NO:21:

(i) SEQUENCE CHARACTERISTICS:
        (A) LENGTH: 26 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:21:

Glu Arg Arg Arg Gly Lys Gly His Asp Gly Leu Tyr Gln Gly Leu Ser
1               5                   10                  15
Thr Ala Thr Lys Asp Thr Tyr Asp Ala Leu
            20                  25

(2) INFORMATION FOR SEQ ID NO:22:

(i) SEQUENCE CHARACTERISTICS:
        (A) LENGTH: 26 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:22:

Glu Arg Arg Arg Gly Lys Gly His Asp Gly Leu Tyr Gln Gly Leu Ser
1               5                   10                  15
Thr Ala Thr Lys Asp Thr Tyr Asp Ala Leu
            20                  25

(2) INFORMATION FOR SEQ ID NO:23:

(i) SEQUENCE CHARACTERISTICS:
            (A) LENGTH: 27 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:23:

Asn Lys Glu Arg Pro Pro Pro Val Pro Asn Pro Asp Tyr Glu Pro Ile
1               5                   10                  15

Arg Lys Gly Gln Arg Asp Leu Tyr Ser Gly Leu
            20                  25

(2) INFORMATION FOR SEQ ID NO:24:

(i) SEQUENCE CHARACTERISTICS:
            (A) LENGTH: 27 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:24:

Asn Lys Glu Arg Pro Pro Pro Val Pro Asn Pro Asp Tyr Glu Pro Ile
1               5                   10                  15

Arg Lys Gly Gln Arg Asp Leu Tyr Ser Gly Leu
            20                  25

(2) INFORMATION FOR SEQ ID NO:25:

(i) SEQUENCE CHARACTERISTICS:
            (A) LENGTH: 27 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:25:

Asn Lys Glu Arg Pro Pro Pro Val Pro Asn Pro Asp Tyr Glu Pro Ile
1               5                   10                  15

Arg Lys Gly Gln Arg Asp Leu Tyr Ser Gly Leu
            20                  25

(2) INFORMATION FOR SEQ ID NO:26:

(i) SEQUENCE CHARACTERISTICS:
            (A) LENGTH: 113 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:26:

Arg Ala Lys Phe Ser Arg Ser Ala Glu Thr Ala Ala Asn Leu Gln Asp
1               5                   10                  15

Pro Asn Gln Leu Tyr Asn Glu Leu Asn Leu Gly Arg Arg Glu Glu Tyr
            20                  25                  30

Asp Val Leu Glu Lys Lys Arg Ala Arg Asp Pro Glu Met Gly Gly Lys
        35                  40                  45

Gln Gln Arg Arg Arg Asn Pro Gln Glu Gly Val Tyr Asn Ala Leu Gln
    50                  55                  60

-continued

Lys Asp Lys Met Ala Glu Ala Tyr Ser Glu Ile Gly Thr Lys Gly Glu
65                  70                  75                  80

Arg Arg Arg Gly Lys Gly His Asp Gly Leu Tyr Gln Gly Leu Ser Thr
            85                  90                  95

Ala Thr Lys Asp Thr Tyr Asp Ala Leu His Met Gln Thr Leu Ala Pro
            100                 105                 110

Arg (2) INFORMATION FOR SEQ ID NO:27:

(i) SEQUENCE CHARACTERISTICS:
        (A) LENGTH: 64 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:27:

Arg Ala Lys Phe Ser Arg Ser Ala Glu Thr Ala Ala Asn Leu Gln Lys
1               5                   10                  15

Asp Lys Met Ala Glu Ala Tyr Ser Glu Ile Gly Thr Lys Gly Glu Arg
                20                  25                  30

Arg Arg Gly Lys Gly His Asp Gly Leu Tyr Gln Gly Leu Ser Thr Ala
            35                  40                  45

Thr Lys Asp Thr Tyr Asp Ala Leu His Met Gln Thr Leu Ala Pro Arg
    50                  55                  60

(2) INFORMATION FOR SEQ ID NO:28:

(i) SEQUENCE CHARACTERISTICS:
        (A) LENGTH: 26 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:28:

Arg Ala Lys Phe Ser Arg Ser Ala Glu Thr Ala Ala Asn Leu Gln Ala
1               5                   10                  15

Cys Lys Leu Met Gln Thr Leu Ala Pro Arg
                20                  25

(2) INFORMATION FOR SEQ ID NO:29:

(i) SEQUENCE CHARACTERISTICS:
        (A) LENGTH: 53 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:29:

Arg Ala Lys Phe Ser Arg Ser Ala Glu Thr Ala Ala Asn Leu Gln Gly
1               5                   10                  15

Thr Lys Gly Glu Arg Arg Arg Gly Lys Gly His Asp Gly Leu Tyr Gln
                20                  25                  30

Gly Leu Ser Thr Ala Thr Lys Asp Thr Tyr Asp Ala Leu His Met Gln
            35                  40                  45

Thr Leu Ala Pro Arg
    50

(2) INFORMATION FOR SEQ ID NO:30:

(i) SEQUENCE CHARACTERISTICS:
        (A) LENGTH: 113 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:30:

```
Arg Ala Lys Phe Ser Arg Ser Ala Glu Thr Ala Ala Asn Leu Gln Asp
1               5                   10                  15

Pro Asn Gln Leu Tyr Asn Glu Leu Asn Leu Gly Arg Arg Glu Glu Tyr
            20                  25                  30

Asp Val Leu Glu Lys Lys Arg Ala Arg Asp Pro Glu Met Gly Gly Lys
        35                  40                  45

Gln Gln Arg Arg Arg Asn Pro Gln Glu Gly Val Tyr Asn Ala Leu Gln
    50                  55                  60

Lys Asp Lys Met Ala Glu Ala Tyr Ser Glu Ile Gly Thr Lys Gly Glu
65                  70                  75                  80

Arg Arg Arg Gly Lys Gly His Asp Gly Leu Tyr Gln Gly Leu Ser Thr
                85                  90                  95

Ala Thr Lys Asp Thr Glu Asp Ala Leu His Met Gln Thr Leu Ala Pro
            100                 105                 110

Arg
```

(2) INFORMATION FOR SEQ ID NO:31:

(i) SEQUENCE CHARACTERISTICS:
        (A) LENGTH: 113 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:31:

```
Arg Ala Lys Phe Ser Arg Ser Ala Glu Thr Ala Ala Asn Leu Gln Asp
1               5                   10                  15

Pro Asn Gln Leu Tyr Asn Glu Leu Asn Leu Gly Arg Arg Glu Glu Tyr
            20                  25                  30

Asp Val Leu Glu Lys Lys Arg Ala Arg Asp Pro Glu Met Gly Gly Lys
        35                  40                  45

Gln Gln Arg Arg Arg Asn Pro Gln Glu Gly Val Tyr Asn Ala Leu Gln
    50                  55                  60

Lys Asp Lys Met Ala Glu Ala Tyr Ser Glu Ile Gly Thr Lys Gly Glu
65                  70                  75                  80

Arg Arg Arg Gly Lys Gly His Asp Gly Leu Tyr Gln Gly Leu Ser Thr
                85                  90                  95

Ala Thr Lys Asp Thr Phe Asp Ala Leu His Met Gln Thr Leu Ala Pro
            100                 105                 110

Arg
```

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following claims:

What is claimed is:

1. A method to identify compounds capable of regulating T cell activation-associated association between a T cell receptor and actin in a mature T lymphocyte, comprising:

(a) contacting a putative regulatory compound with a mature T lymphocyte having a cytoskeleton comprising actin and a T cell receptor chain selected from the group consisting of a zeta (ζ) chain having a first, second and third immunoreceptor tyrosine-based activation motif (ITAM) and an epsilon (ε) chain having an ITAM, to form a contacted lymphocyte;

(b) stimulating said T lymphocyte with a stimulatory molecule such that the phosphorylation of tyrosine residues in said third ITAM of said zeta chain or said ITAM of said epsilon chain occurs; and (c) assessing the ability of said putative regulatory compound to regulate an association between said actin and said third ITAM of said zeta chain or said ITAM of said epsilon chain a compared to a mature T lymphocyte that has not been contacted with said putative regulatory compound by a predeterminative step selected from the group consisting of: (1) isolating by sedimentation said actin, and detecting actin association with said third ITAM of said ζ chain or said ITAM of said epsilon chain using an antibody that specifically binds to said ζ or ε chain; and, (2) isolating said ζ or ε chain and detecting actin association with said third ITAM of said ζ chain or said ITAM of said epsilon chain using an antibody that specifically binds to said actin.

2. The method of claim 1, further comprising step (d) of assessing the amount of interleukin-2 produced by said lymphocyte.

3. The method of claim 1, wherein said step of contacting comprises administering said putative regulatory compound by a technique selected from the group consisting of electroporation, microinjection, cellular expression, use of ion carrying agents and use of detergents for cell permeabilization.

4. The method of claim 3, wherein said cellular expression is accomplished using an expression system selected from the group consisting of naked nucleic acid molecules, recombinant virus, retrovirus expression vectors and adenovirus expression vectors.

5. The method of claim 1, wherein said stimulatory molecule is selected from the group consisting of an antibody specific for a T cell receptor, an antibody specific for said ζ chain, an antibody specific for said ε chain, mitogens, lectins and major histocompatibility molecules associated with an antigenic peptide.

6. The method of claim 1, further comprising step (d) of determining whether said lymphocyte has undergone a change in homing activity.

7. The method of claim 1, further comprising step (d) of determining apoptosis of said mature T lymphocyte.

8. The method of claim 1, wherein said mature T lymphocyte is selected from the group consisting of T cell lines, T cell clones and T cell hybridomas.

9. The method of claim 1, wherein said third ITAM of said zeta chain comprises the amino acid sequence SEQ ID NO:1, and wherein said ITAM of said epsilon chain comprises the amino acid sequence SEQ ID NO:2.

10. The method of claim 1, further comprising step (d) of detecting actin polymerization in said contacted mature T lymphocyte compared to a mature T lymphocyte that has not been contacted with said putative regulatory compound.

11. The method of claim 10, wherein said step of detecting actin polymerization comprises determining whether said lymphocyte has undergone a morphological change, said change selected from the group consisting of changes in adhesion, growth, shape and motility characteristics.

12. The method of claim 10, wherein said step of detecting actin polymerization comprises determining the modulation of a molecule selected from the group consisting of focal adhesion kinase, paxillin, vinculin, tensin, PI-3Kα, TCR, Syk, Zap-70, Fyn, Shc, IRS-1, Nck, Lck, VAV, GAP, Raf, MEK, MEKK, MAPK, p38, JNKK, JNK, PLA2, JAK1, JAK2, JAK3, Tyk1, Tyk2, STATs, Myc, Jun, Ets-1, Elk-1, CREB, ATF-2, Yes, Hck, Src, CaM Kinase II, S6-K, sphingamyelinase, casein kinase, PKC, PI-3Kγ, SOS, CD45, HCP, Ssp, Syp, PLCγ1, PLCγ2, PLCβ1, PLCβ2, PLCβ3, PLCβ4, PLA2, Grb2, C5aR, IL-8R, MIP1αR, MIP1βR, MCP-1R, MCP-3R, PAFR, FMLPR, LTB$_4$R, GRPR, and Fas receptor.

13. The method of claim 10, wherein an increase or decrease in actin polymerization in said contacted mature T lymphocyte compared to said mature T lymphocyte that has not been contacted with said putative regulatory compound indicates that said regulatory compound is capable of regulating T cell activation.

14. A kit to identify compounds capable of regulating T cell activation-associated association between a T cell receptor and actin of a mature T lymphocyte, said kit comprising:

(a) a cell comprising actin selected from the group consisting of actin monomers, actin diners and short filaments thereof, and a T cell receptor chain selected from the group consisting of a ζ chain having a first, second and third immunoreceptor tyrosine-based activation motif (ITAM) and an chain having an ITAM;

(b) a stimulatory molecule which binds to cell surface receptors of said cell to initiate a signal transduction pathway such that the phosphorylation of tyrosine residues of said ITAM occurs;

(c) an antibody that specifically binds to actin for detecting an association between said actin and said third ITAM of said ζ chain or said ITAM of said ε chain; and, (d) an antibody selected from the group consisting of an antibody that specifically binds to said ζ chain and an antibody that specifically binds to said ε chain for detecting an association between said actin and said third ITAM of said ζ chain or said ITAM of said ε chain.

15. The kit of claim 14, wherein said cell is selected from the group consisting of Jurkat cells, MM-16.12 cells, 17.2 cells, 17.4 cells, 122.26 cells, HL-60 cells, H-9 cells, peripheral T cells, PBMC cells, lymph node T cells, splenic T cells, thymocytes, intraepithelial lymphocytes and tumor infiltrating lymphocytes.

16. A method to identify compounds capable of regulating T cell activation-associated association between actin and a T cell receptor of a mature T lymphocyte, comprising:

(a) contacting a putative regulatory compound with a mature T lymphocyte to form a contacted lymphocyte, said mature T lymphocyte having a cytoskeleton comprising actin and a phosphorylated T cell receptor zeta (ζ) chain having a first, second and third immunoreceptor tyrosine-based activation motif (ITAM);

(b) stimulating said T lymphocyte with a stimulatory molecule such that the phosphorylation of tyrosine residues of said third ITAM of said zeta chain occurs; and, (c) assessing the ability of said putative regulatory compound to regulate an association between said actin and said third ITAM of said zeta chain as compared to a mature T lymphocyte that has not been contacted with said putative regulatory compound by a determinative step selected from the group consisting of: (1) isolating by sedimentation said actin, and detecting actin association with said third ITAM of said ζ chain using an antibody that specifically binds to said ζ chain; and (2)

isolating said ζ chain and detecting actin association with said third ITAM of said ζ chain using an antibody that specifically binds to said actin.

17. A method to identify compounds capable of regulating T cell activation-associated association between actin and a T cell receptor of a mature T lymphocyte, comprising:
   (a) contacting a putative regulatory compound with a mature T lymphocyte to form a contacted lymphocyte, said mature T lymphocyte having a cytoskeleton comprising actin and a phosphorylated T cell receptor epsilon (ε) chain having an immunoreceptor tyrosine-based activation motif (ITAM);
   (b) stimulating said T lymphocyte with a stimulatory molecule such that the phosphorylation of tyrosine residues of said ITAM of said epsilon chain occurs; and,
   (c) assessing the ability of said putative regulatory compound to regulate an association between said actin and said ITAM of said epsilon chain zeta chain as compared to a mature T lymphocyte that has not been contacted with said putative regulatory compound by a determinative step selected from the group consisting of: (1) isolating by sedimentation said actin, and detecting actin association with said ITAM of said ε chain using an antibody that specifically binds to said ε chain; and, (2) isolating said ε chain and detecting actin association with said ITAM of said ε chain using an antibody that specifically binds to said actin.

18. A method to identify compounds capable of regulating cell-activation associated association between actin and a multisubunit immune recognition receptor (MIRR) in a cell, comprising:
   (a) contacting a putative regulatory compound with a cell to form a contacted cell, said cell having a cytoskeleton comprising actin and a multisubunit immune recognition receptor (MIRR) selected from the group consisting of a T cell receptor, a B cell antigen receptor, an Fc receptor, and CD22;
   said MIRR having an immunoreceptor tyrosine-based activation motif (ITAM);
   (b) stimulating said cell with a stimulatory molecule such that the phosphorylation of tyrosine residues of said ITAM of said MIRR occurs; and
   (c) assessing the ability of said putative regulatory compound to regulate an association between said actin and said ITAM of said MIRR zeta chain as compared to a cell that has not been contacted with said putative regulatory compound by a determinative step selected from the group consisting of: (1) isolating by sedimentation said actin, and detecting actin association with said ITAM of said MIRR chain using an antibody that specifically binds to said MIRR chain; and, (2) isolating said MIRR chain and detecting actin association with said ITAM of said MIRR chain using an antibody that specifically binds to said actin.

19. A method to identify compounds capable regulating T cell activation-associated association between a T cell receptor and actin in a mature T lymphocyte, comprising:
   (a) contacting a putative regulatory compound with a mature T lymphocyte having a cytoskeleton comprising actin and a T cell receptor chain selected from the group consisting of a zeta (ζ) chain having a first, second and third immunoreceptor tyrosine-based activation motif (ITAM) and an epsilon (ε) chain having an ITAM, to form a contacted lymphocyte;
   wherein said third ITAM of said zeta chain and said ITAM of said epsilon chain each have a distal tyrosine residue;
   (b) stimulating said T lymphocyte with a stimulatory molecule such that phosphorylation of said tyrosine residues of said third ITAM of said zeta chain or said ITAM of said epsilon chain occurs; and
   (c) assessing the ability of said putative regulatory compound to regulate an association between said actin and said distal tyrosine residue of said third ITAM of said zeta chain or of said ITAM of said epsilon chain as compared to a mature T lymphocyte that has not been contacted with said putative regulatory compound by a determinative step selected from the group consisting of: (1) isolating by sedimentation said actin, and detecting actin association with said distal tyrosine residue of said third ITAM of said ζ chain or of said ITAM of said epsilon chain using an antibody that specifically binds to said ζ or ε chain; and, (2) isolating said ζ or ε chain and detecting actin association with said distal tyrosine residue of said third ITAM of said ζ chain or of said ITAM of said epsilon chain using an antibody that specifically binds to said actin.

20. A method to identify compounds capable of regulating T cell activation-associated association between actin and a T cell receptor of a mature T lymphocyte, comprising:
   (a) contacting a putative regulatory compound with a mature T lymphocyte to form a contacted lymphocyte, said mature T lymphocyte having a cytoskeleton comprising actin and a phosphorylated T cell receptor zeta (ζ) chain having a first, second and third immunoreceptor tyrosine-based activation motif (ITAM);
   wherein said third ITAM of said zeta chain has a distal tyrosine residue;
   (b) stimulating said T lymphocyte with a stimulatory molecule such that phosphorylation of said tyrosine residues of said third ITAM of said zeta chain occurs; and,
   (c) assessing the ability of said putative regulatory compound to regulate an association between said actin and said distal tyrosine residue of said third ITAM of said zeta chain as compared to a mature T lymphocyte that has not been contacted with said putative regulatory compound by a determinative step selected from the group consisting of: (1) isolating by sedimentation said actin, and detecting actin association with said distal tyrosine residue of said third ITAM of said ζ chain using an antibody that specifically binds to said ζ chain; and, (2) isolating said ζ chain and detecting actin association with said distal tyrosine residue of said third ITAM of said ζ chain using an antibody that specifically binds to said actin.

21. A method to identify compounds capable of regulating T cell activation-associated association between actin and a T cell receptor of a mature T lymphocyte, comprising:
   (a) contacting a putative regulatory compound with a mature T lymphocyte to form a contacted lymphocyte, said mature T lymphocyte having a cytoskeleton comprising actin and a phosphorylated T cell receptor epsilon (ε) chain having an immunoreceptor tyrosine-based activation motif (ITAM);
   wherein said ITAM of said epsilon chain has a distal tyrosine residue;
   (b) stimulating said T lymphocyte with a stimulatory molecule such that phosphorylation of said tyrosine residues of said ITAM of said epsilon chain occurs; and,
   (c) assessing the ability of said putative regulatory compound to regulate an association between said actin and said distal tyrosine residue of said ITAM of said epsilon chain as compared to a mature T lymphocyte that has not been contacted with said putative regulatory compound by a determinative step selected from the group consisting of: (1) isolating by sedimentation said actin, and detecting actin association with said distal tyrosine residue of said ITAM of said $\epsilon$ chain using an antibody that specifically binds to said $\epsilon$ chain; and, (2) isolating said $\epsilon$ chain and detecting actin association with said distal tyrosine residue of said ITAM of said $\epsilon$ chain using an antibody that specifically binds to said actin.

22. A method to identify compounds capable of regulating cell-activation associated association between actin and a multisubunit immune recognition receptor (MIRR) in a cell, comprising:

(a) contacting a putative regulatory compound with a cell to form a contacted cell, said cell having a cytoskeleton comprising actin and a multisubunit immune recognition receptor (MIRR) selected from the group consisting of a T cell receptor, a B cell antigen receptor, an Fc receptor, and CD22;

said MIRR having an immunoreceptor tyrosine-based activation motif (ITAM), wherein said ITAM of said MIRR has a distal tyrosine residue;

(b) stimulating said cell with a stimulatory molecule such that the phosphorylation of said tyrosine residues of said ITAM of said MIRR occurs; and (c) assessing the ability of said putative regulatory compound to regulate an association between said actin and said distal tyrosine residue of said ITAM of said MIRR as compared to a cell that has not been contacted with said putative regulatory compound by a determinative step selected from the group consisting of: (1) isolating by sedimentation said actin, and detecting actin association with said distal tyrosine residue of said ITAM of said MIRR chain using an antibody that specifically binds to said MIRR chain; and, (2) isolating said MIRR chain and detecting actin association with said distal tyrosine residue of said ITAM of said MIRR chain using an antibody that specifically binds to said actin.

* * * * *

UNITED STATES PATENT AND TRADEMARK OFFICE
CERTIFICATE OF CORRECTION

PATENT NO. : 5,976,819
DATED : November 2, 1999
INVENTOR(S) : Finkel et al.

It is certified that error appears in the above-identified patent and that said Letters Patent is hereby corrected as shown below:

Column 41,
Line 15, delete "predeterminative" and insert -- determinative -- therefor;

Column 42,
Line 6, delete "sphingamyelinase" and insert -- sphingomyelinase -- therefor;
Line 21, delete "diners" and insert -- dimers -- therefor;
Line 25, insert -- $\epsilon$ -- before the word "chain"

Signed and Sealed this

Seventh Day of January, 2003

JAMES E. ROGAN
*Director of the United States Patent and Trademark Office*